US011202559B2

(12) United States Patent
Mulcahey et al.

(10) Patent No.: US 11,202,559 B2
(45) Date of Patent: Dec. 21, 2021

(54) VISION PRESERVATION SYSTEM FOR MEDICAL DEVICES

(71) Applicant: CSA Medical, Inc., Lexington, MA (US)

(72) Inventors: Thomas Mulcahey, Belmont, MA (US); Daniel J. Grasso, Roslindale, MA (US); David Sherrill, Westford, MA (US)

(73) Assignee: CSA Medical, Inc., Lexington, MA (US)

( * ) Notice: Subject to any disclaimer, the term of this patent is extended or adjusted under 35 U.S.C. 154(b) by 730 days.

(21) Appl. No.: 15/498,439

(22) Filed: Apr. 26, 2017

(65) Prior Publication Data
US 2017/0311789 A1 Nov. 2, 2017

Related U.S. Application Data

(60) Provisional application No. 62/328,044, filed on Apr. 27, 2016.

(51) Int. Cl.
*A61B 1/12* (2006.01)
*A61B 1/00* (2006.01)
(Continued)

(52) U.S. Cl.
CPC .......... *A61B 1/126* (2013.01); *A61B 1/00091* (2013.01); *A61B 1/00101* (2013.01);
(Continued)

(58) Field of Classification Search
CPC .......... A61B 1/127; A61B 1/126; A61B 1/12; A61B 1/015; A61B 1/00137;
(Continued)

(56) References Cited

U.S. PATENT DOCUMENTS 3,630,203 A 12/1971 Sellinger
3,782,386 A 1/1974 Barger et al.
(Continued)

FOREIGN PATENT DOCUMENTS

DE 10024728 11/2001
JP S54107191 A 8/1979
(Continued)

OTHER PUBLICATIONS

International Search Report and Written Opinion dated (Oct. 9, 2017), for PCT/US17/29722 (17 pages).
(Continued)

*Primary Examiner* — John P Leubecker
(74) *Attorney, Agent, or Firm* — Kacvinsky Daisak Bluni PLLC

(57) ABSTRACT

The present disclosure includes vision preservation systems for medical devices, such as cryospray devices for use with endoscopes. Exemplary embodiments provide a distal attachment in the form of a shroud or cap that mounts to the end of a flexible endoscope. A purging fluid supply mechanism is provided along the length of the endoscope, providing a channel for purging fluid, such as gas, to communicate between the endoscope tip and an external gas supply. The cap or shroud assembly incorporates a lens clearing flow field adjustment mechanism, such as nozzles, designed to direct warm (room temperature or higher) purging fluid across a lens at the scope tip. Another flow deflection mechanism, such as a guide or nozzle, may be included with the cap to direct purging fluid at an angle away from the lens.

17 Claims, 29 Drawing Sheets

(51) Int. Cl.
  *A61B 18/02* (2006.01)
  *A61F 7/00* (2006.01)
  *A61B 1/018* (2006.01)
  *A61F 7/12* (2006.01)
  *A61B 1/015* (2006.01)

(52) U.S. Cl.
  CPC ...... *A61B 1/00137* (2013.01); *A61B 1/00195* (2013.01); *A61B 1/018* (2013.01); *A61B 1/127* (2013.01); *A61B 18/02* (2013.01); *A61B 18/0218* (2013.01); *A61F 7/007* (2013.01); *A61F 7/12* (2013.01); *A61B 1/015* (2013.01); *A61B 1/128* (2013.01); *A61B 2018/0212* (2013.01); *A61F 2007/0059* (2013.01); *A61F 2007/0063* (2013.01); *A61F 2007/0071* (2013.01); *A61F 2007/0086* (2013.01)

(58) Field of Classification Search
  CPC ............ A61B 1/00091; A61B 1/00089; A61B 1/00101; A61B 1/00094; A61B 2018/0212
  See application file for complete search history.

(56) References Cited

U.S. PATENT DOCUMENTS

| | | | |
|---|---|---|---|
| 4,146,030 A | 3/1979 | Holroyd | |
| 5,313,934 A | 5/1994 | Wiita et al. | |
| 5,339,800 A * | 8/1994 | Wiita | A61B 1/00091 600/109 |
| 5,386,817 A * | 2/1995 | Jones | A61B 1/00091 138/108 |
| 5,464,008 A * | 11/1995 | Kim | A61B 1/00091 600/157 |
| 5,536,236 A * | 7/1996 | Yabe | A61B 1/00089 600/125 |
| 5,720,764 A | 2/1998 | Naderlinger | |
| 5,846,235 A | 12/1998 | Pasricha et al. | |
| 6,143,013 A | 11/2000 | Samson et al. | |
| 6,237,355 B1 | 5/2001 | Li | |
| 6,287,304 B1 | 9/2001 | Eggers et al. | |
| 6,306,129 B1 | 10/2001 | Little et al. | |
| 6,319,248 B1 | 11/2001 | Nahon | |
| 6,409,657 B1 * | 6/2002 | Kawano | A61B 1/00091 600/127 |
| 6,464,716 B1 | 10/2002 | Dobak, III et al. | |
| 6,468,268 B1 | 10/2002 | Abboud et al. | |
| 6,551,309 B1 | 4/2003 | LePivert | |
| 6,712,757 B2 | 3/2004 | Becker et al. | |
| 6,887,234 B2 | 5/2005 | Abboud et al. | |
| 7,025,762 B2 | 4/2006 | Johnston et al. | |
| 7,331,948 B2 | 2/2008 | Skarda | |
| 7,341,556 B2 | 3/2008 | Shalman | |
| 7,507,233 B2 | 3/2009 | Littrup et al. | |
| 7,785,289 B2 | 8/2010 | Rios et al. | |
| 7,991,948 B2 | 8/2011 | Levine | |
| 8,047,215 B1 * | 11/2011 | Sasaki | A61B 1/00135 134/102.1 |
| 2002/0143323 A1 | 10/2002 | Johnston et al. | |
| 2004/0024392 A1 | 2/2004 | Lewis et al. | |
| 2004/0260149 A1 * | 12/2004 | Ishibiki | A61B 1/00089 600/127 |
| 2005/0081541 A1 | 4/2005 | Copping | |
| 2005/0283136 A1 | 12/2005 | Skarda | |
| 2006/0062895 A1 | 3/2006 | Pursley | |
| 2006/0281973 A1 | 12/2006 | Sugita | |
| 2007/0066870 A1 * | 3/2007 | Ohashi | A61B 1/00089 600/127 |
| 2007/0123852 A1 | 5/2007 | Deem et al. | |
| 2007/0129719 A1 * | 6/2007 | Kendale | A61B 1/313 606/41 |
| 2007/0177008 A1 | 8/2007 | Bayer et al. | |
| 2007/0233055 A1 | 10/2007 | Abboud et al. | |
| 2007/0253463 A1 | 11/2007 | Perry et al. | |
| 2007/0282253 A1 * | 12/2007 | Sasaki | A61B 1/00091 604/93.01 |
| 2007/0293726 A1 * | 12/2007 | Goldfarb | A61B 1/0014 600/178 |
| 2008/0081948 A1 * | 4/2008 | Weisenburgh | A61B 1/00135 600/121 |
| 2008/0188715 A1 * | 8/2008 | Fujimoto | A61B 1/00091 600/157 |
| 2008/0312644 A1 | 12/2008 | Fourkas et al. | |
| 2008/0319266 A1 * | 12/2008 | Poll | A61B 1/00091 600/157 |
| 2009/0078875 A1 | 3/2009 | Rousso et al. | |
| 2009/0157002 A1 | 6/2009 | Dumot et al. | |
| 2009/0192505 A1 | 7/2009 | Askew et al. | |
| 2009/0207494 A1 * | 8/2009 | Gelbart | A61B 1/126 359/509 |
| 2009/0247831 A1 * | 10/2009 | Miyamoto | A61B 1/00135 600/157 |
| 2009/0253965 A1 * | 10/2009 | Miyamoto | A61B 1/00091 600/157 |
| 2010/0010310 A1 * | 1/2010 | Weisenburgh, II | A61B 1/00091 600/156 |
| 2010/0057065 A1 | 3/2010 | Krimsky | |
| 2010/0057067 A1 | 3/2010 | Baust et al. | |
| 2010/0191052 A1 * | 7/2010 | Surti | A61B 1/0014 600/106 |
| 2010/0191232 A1 | 7/2010 | Boveda | |
| 2010/0324483 A1 | 12/2010 | Rozenberg et al. | |
| 2011/0106074 A1 | 5/2011 | Kunis et al. | |
| 2011/0112363 A1 * | 5/2011 | Koga | A61B 1/127 600/109 |
| 2011/0144524 A1 | 6/2011 | Fish et al. | |
| 2011/0208166 A1 | 8/2011 | Dumot et al. | |
| 2011/0319716 A1 * | 12/2011 | Naito | A61B 1/00091 600/157 |
| 2012/0071724 A1 * | 3/2012 | Hashido | A61B 1/00089 600/175 |
| 2012/0226104 A1 * | 9/2012 | Ikeda | A61B 1/126 600/129 |
| 2012/0316394 A1 * | 12/2012 | Yoshida | A61B 1/00091 600/123 |
| 2013/0110098 A1 | 5/2013 | Lalonde | |
| 2013/0204068 A1 | 8/2013 | Gnanashanmugam et al. | |
| 2013/0211198 A1 * | 8/2013 | Torisawa | A61B 1/00089 600/157 |
| 2013/0218149 A1 | 8/2013 | Braun et al. | |
| 2013/0231651 A1 | 9/2013 | Burr et al. | |
| 2014/0018788 A1 | 1/2014 | Engelman et al. | |
| 2014/0058204 A1 | 2/2014 | Ideda et al. | |
| 2014/0148647 A1 * | 5/2014 | Okazaki | A61B 1/00091 600/154 |
| 2015/0066005 A1 | 3/2015 | Fan et al. | |
| 2015/0182108 A1 * | 7/2015 | Fukuda | A61B 1/00135 600/157 |
| 2015/0250524 A1 | 9/2015 | Moriarty et al. | |
| 2016/0309994 A1 * | 10/2016 | Kuwae | A61B 1/00091 |

FOREIGN PATENT DOCUMENTS

| | | |
|---|---|---|
| JP | H10127567 A | 5/1998 |
| JP | 200217651 A | 12/2009 |
| JP | 2009279291 A | 12/2009 |
| JP | 2011120863 A | 6/2011 |
| JP | 2012120701 A | 6/2012 |
| JP | 3186191 U | 9/2013 |
| JP | 2013169380 A | 9/2013 |
| JP | 5456710 B2 | 4/2014 |
| JP | 2016508820 A | 3/2016 |
| WO | 9204872 A1 | 4/1992 |
| WO | 9915093 A1 | 4/1999 |
| WO | 0101049 A1 | 1/2001 |
| WO | 0211638 A1 | 2/2002 |
| WO | 2009082433 A2 | 7/2009 |

(56) References Cited

FOREIGN PATENT DOCUMENTS

| WO | 2009095915    | 8/2009  |
|----|---------------|---------|
| WO | 2009140067 A1 | 11/2009 |
| WO | 2012006408 A1 | 1/2012  |

OTHER PUBLICATIONS

International Search Report dated (Mar. 11, 2014, for PCT/US13/57037 (4 pages).
T J Lynch, Polyimide Tubing: Dispelling the Myths, Microlumen, http://www.microlumen.com/news/industry-news/18-polyimide-tubing-dispelling-the-myths.

* cited by examiner

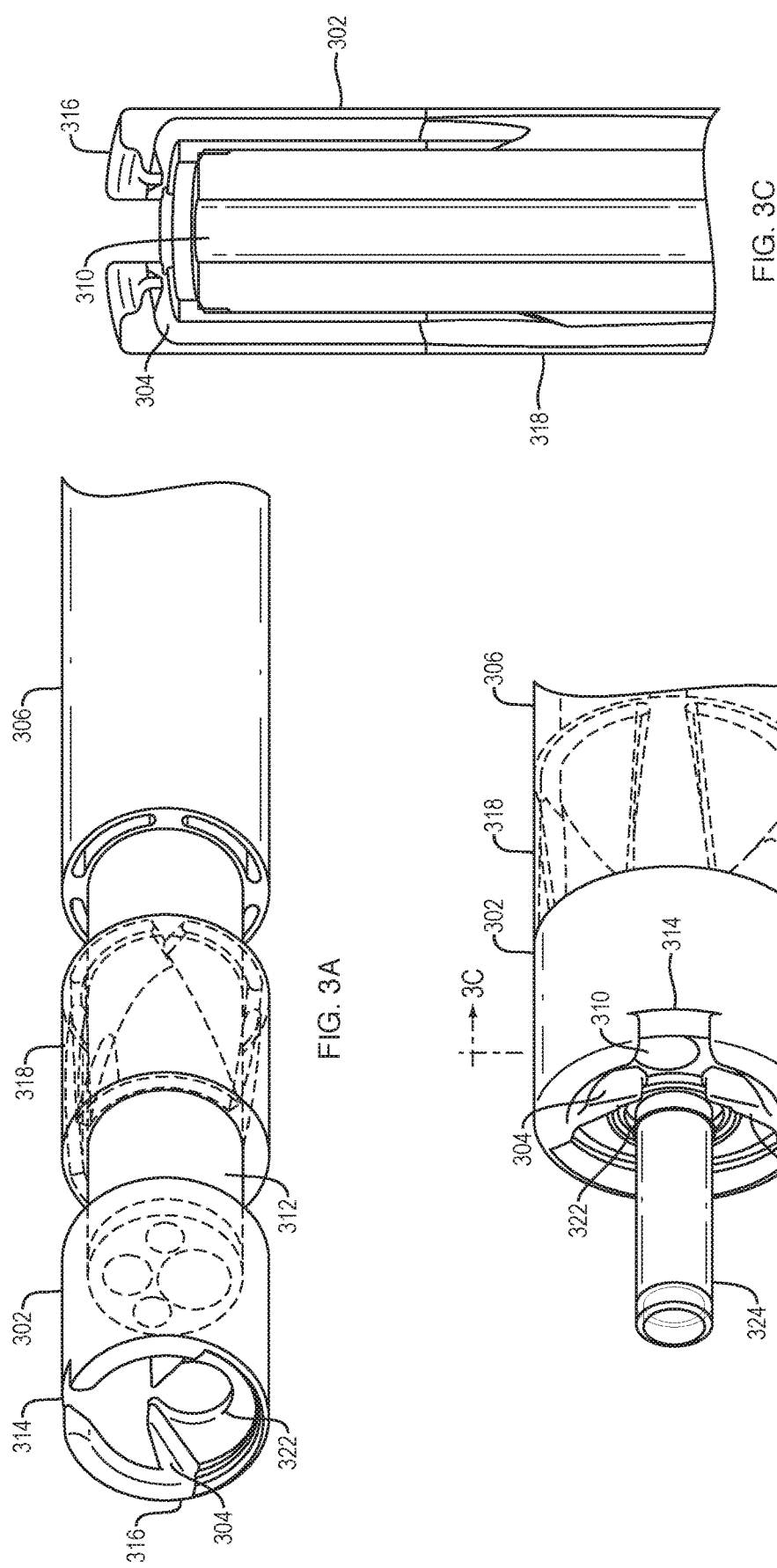

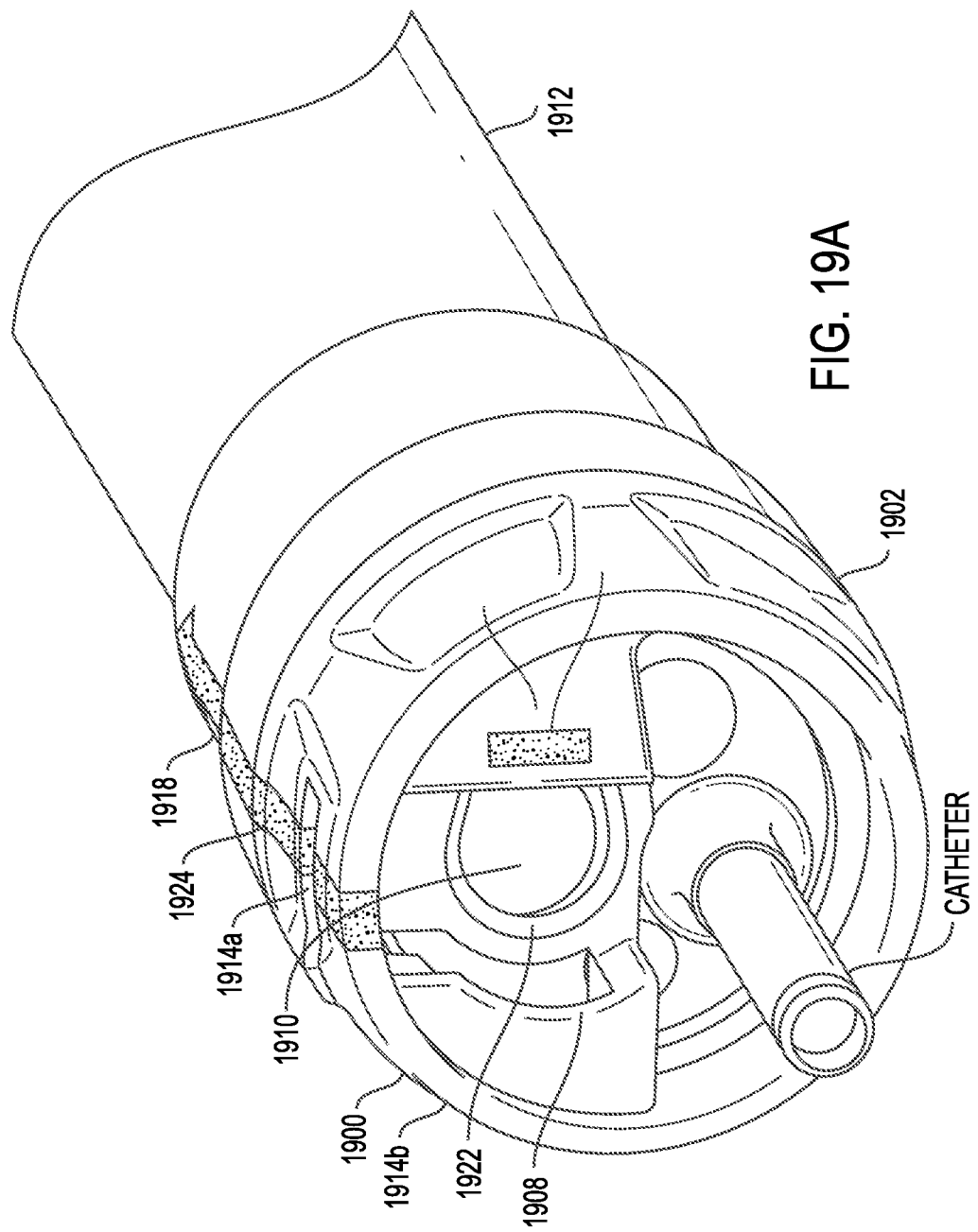

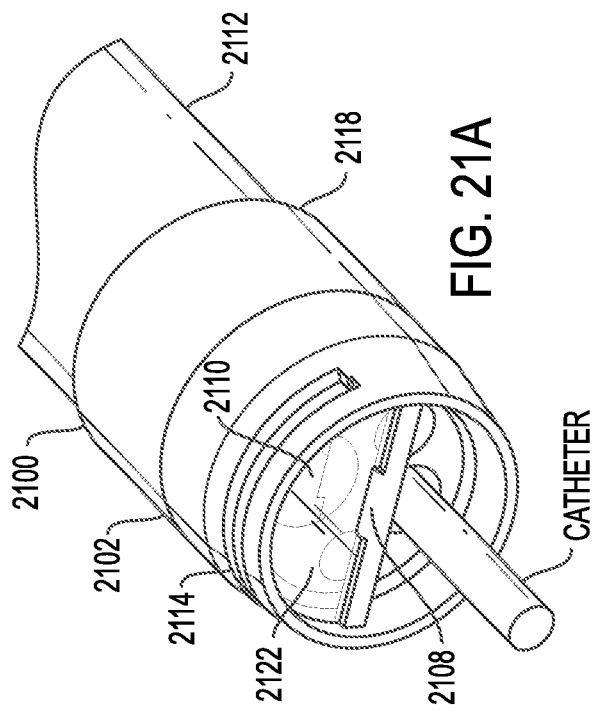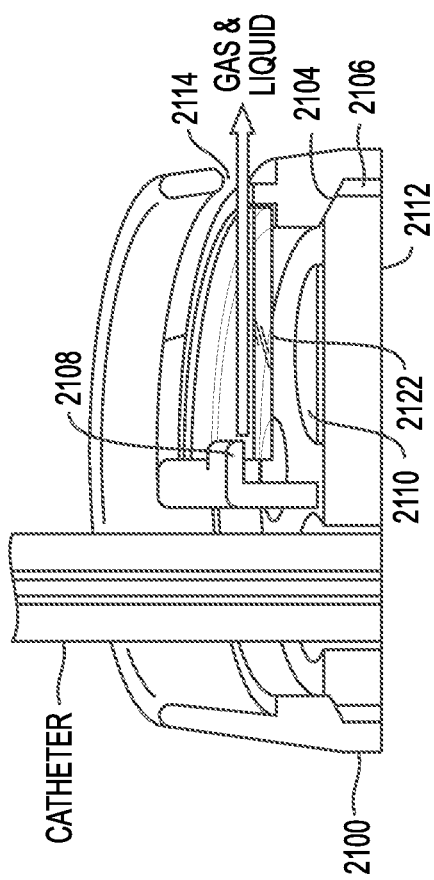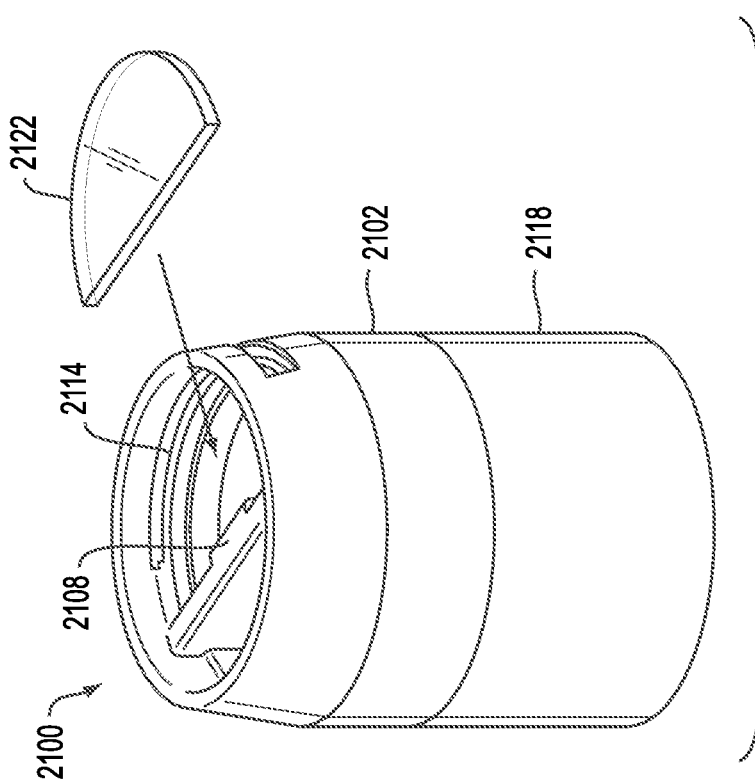

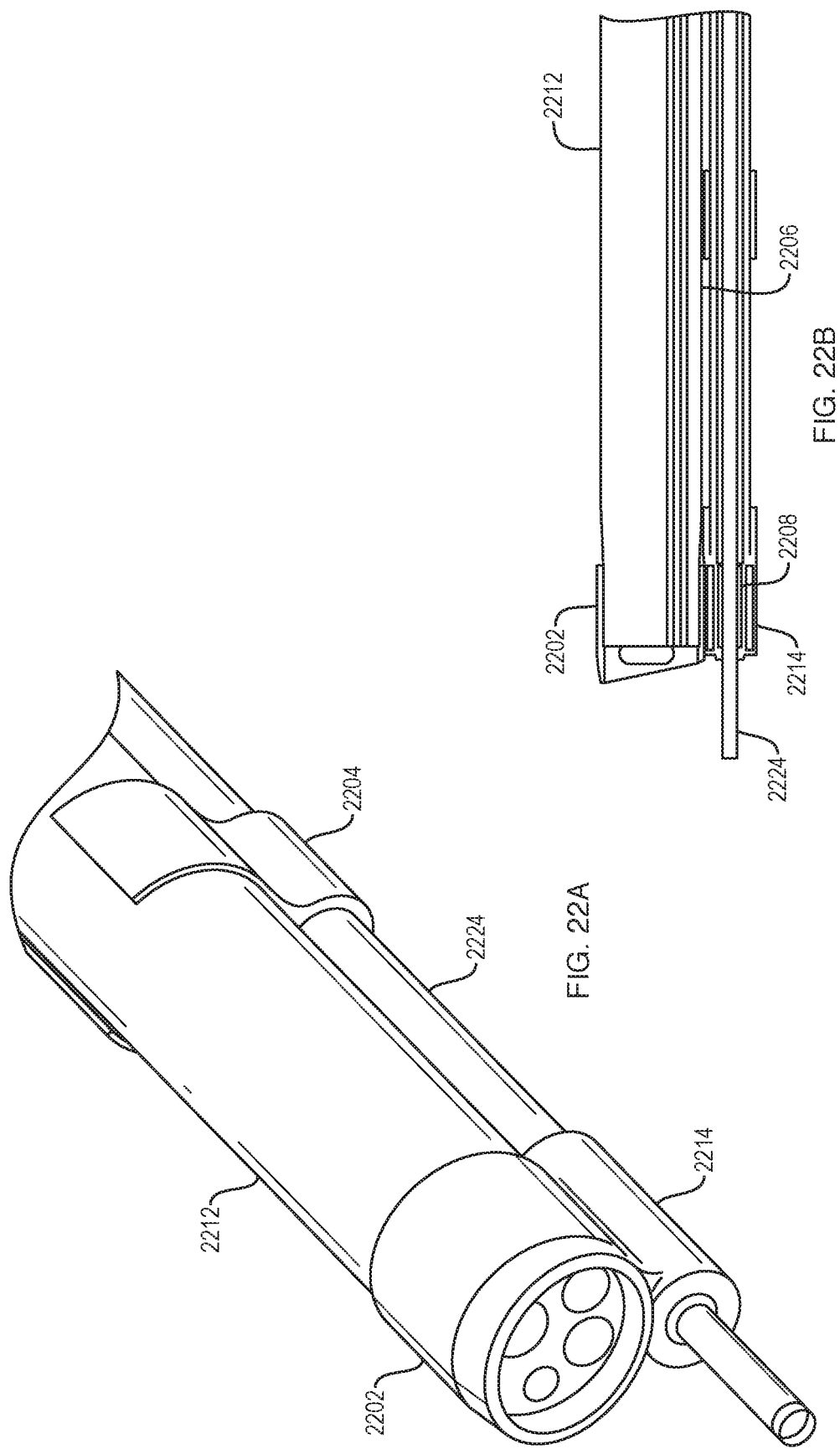

VISION PRESERVATION SYSTEM FOR MEDICAL DEVICES

PRIORITY

This application claims the benefit of priority under 35 U.S.C. § 119 to U.S. Provisional Patent Application Ser. No. 62/328,044, filed Apr. 27, 2016, which is incorporated by reference in its entirety and for all purposes.

FIELD OF THE INVENTION

The present invention relates to vision preservation systems for medical devices, and particularly for endoscopes and cryospray devices.

BACKGROUND

The primary purpose of an endoscope, video or fiber optic, is to provide visualization of anatomical lumens for either exploratory, diagnostic or interventional procedures. Visibility may be compromised when the distal tip of the scope containing the imaging device, such as charge-coupled device (CCD) capsule or fiber optic lens cover, becomes blocked. This blockage may result from any of several processes, such as: a room temperature endoscope is introduced into a warm, humid body cavity or lumen containing gas with a dew point higher than the lens cover, causing moisture to condense or "fog" on the lens (which may cause a whiteout condition in which visibility becomes severely restricted), or causing drops to impact or build-up on the lens cover (spatter); bodily fluids are put into contact with the lens cover during navigation or as a result of flow field disturbances such as those present in spray cryotherapy, ultrasonic cutting, insufflation, among others; or fog (cryo) or smoke (cutting/thermal ablation) in the target lumen impedes the visual path to the tissue.

A number of products are currently marketed in an attempt to address the above issues. One class of products are marketed as "anti-fog" solutions, which consist of a surfactant applied to the lens cover via a cloth, sponge, or bath. The mechanism of action for surfactants is to break the surface tension of droplets which form due to condensation or spatter on the lens cover, causing the fluid to spread into a more even film which reduces visual impairment. However, such surfactants typically provide no protection against lens spatter, and furthermore must be reapplied regularly (potentially requiring that the endoscope be removed from the patient before a procedure is complete).

Another class of marketed products preheats the endoscope prior to patient insertion to avoid condensing moisture on the lens cover. Commercial devices consist of warming packs that deliver energy through an exothermic chemical reaction, and a heated bath of surfactant to preheat and apply anti-fog solution prior to insertion. Some such products also claim that the surfactant bath is used to remove debris, while others use a warming chamber to accept an endoscope for wiping with microfiber cloths and heating, but in each case the endoscope has to be removed from the patient in order to apply heat, receive a wiping, or apply surfactant.

Furthermore, some products provide caps to be applied to endoscopic imaging systems. Examples include various distal caps by Olympus Corporation of Tokyo, Japan, and the Halo Cap by Barrx Medical of Sunnyvale, Calif., now Medtronic of Fridley, Minn.

SUMMARY

Exemplary embodiments according to the present disclosure provide a distal attachment in the form of a cap or shroud that mounts to the end of a flexible endoscope (e.g., a gastroscope or bronchoscope). Embodiments of the caps provide various mechanisms for delivering moisture and contaminant purging fluid to the cap for improving visual properties at the end of the endoscope. For example, in one embodiment, tubing may be provided along the length of the endoscope, providing a fluid channel in fluid communication between the endoscope tip and an external fluid supply. In another embodiment, supply fluid may also be routed through an internal rinse channel, if available.

A cap and shroud assembly may incorporate one or more lens clearing flow field adjustment mechanisms, such as a nozzle, designed to distribute warm (e.g., room temperature or higher) purging fluid across the lens. Other flow purging mechanisms are designed to direct purging fluid or deflect spatter at an angle away from the lens. In some embodiments, features other than nozzles may create a nozzling or flow guiding effect. The lens clearing flow field adjustment mechanisms may modify or adjust the flow of the purging fluid. Fluid directed across and toward the lens purges moisture to avoid condensation on the lens and shears debris and bodily fluids away from the field of view. The heat of the purging fluid may prevent condensation by keeping the lens above the ambient dew point temperature. Fluid directed away from the lens serves the purpose of deflecting incoming particles and fluid droplets to avoid impact on the lens cover. Embodiments of the cap or shroud are designed to avoid entraining moist air from the body cavity or lumen being treated.

The distal cap attachment serves several purposes. For example, the attachment purges the space adjacent to an endoscope lens cover of moisture to avoid condensation. Further, the cap clears debris from the endoscope lens cover, and deflects incoming matter (spatter) to avoid impact and build-up on the lens that can obscure vision. The cap can also act as a barrier to prevent tissue or mucus from blocking the lens during endoscopic insertion. In cases in which the distal attachment is provided on an endoscope employed in a cryotherapy application, the distal attachment can also serve to warm the distal tip of the endoscope.

Embodiments of the cap may include one or more guides that extend from or around an edge of the cap in proximity to the lens clearing flow field adjustment mechanism in order to direct, deflect, or recycle flow towards the lens and/or a drain, or away from a catheter. Guides may take on many shapes to create a desired path for the purging fluid, such as curves and slants. Guides may also direct and induce turbulent flow distally to the cap and distal end of the endoscope, such as, for example, in a distal vortex to further clear or keep clear the viewing area of obstructions. Guides may include a lumen that extends proximally along the cap and actively and/or passively vents the purging fluid.

Embodiments of the cap may include a seal disposed about a working channel of the endoscope to create a substantially fluid-tight fit for the catheter or other tool such that fluids are inhibited or prevented from entering the working channel of the endoscope, or so that the catheter does not undesirably move around within the working channel.

Embodiments of the visualization system may include a purging fluid supply mechanism that is an outer lumen of a multilumen sheath. An endoscope may slide into an inner lumen of the multilumen sheath and the purging fluid may be supplied to a lens clearing nozzle via the outer lumen. A purging fluid supply mechanism may be an independent supply line or tube attached to the outside of the endoscope.

Embodiments of the system may include heating elements, such as one or more flexible printed circuits, that electrically heat the endoscope, lens, and/or the purging fluid supply mechanism to avoid condensation/freezing temperatures. The heating element may run along the length of the endoscope and/or the purging fluid supply mechanism such that the purging fluid is adequately heated when it reaches the cap. The devices of the system may be heat treated before, during, or in between treatments. Heating may also be performed by a heating sheath, heating wrap, or inline heater. Various types of insulation materials may be incorporated in the systems. Sensors and a power supply for the heating elements may be included for feedback control.

Embodiments of a visualization system may include an endoscope having a lens and a working channel for a tool. A cap may be at least partially surrounding a lens. A system with a cap may include a lens clearing flow field adjustment mechanism for delivering purging fluid to a lens, wherein the cap is sized and configured to reduce entrainment of moisture in the vicinity of the lens. A lens clearing flow field adjustment mechanism may be configured to deliver an angled jet of purging fluid to a lens. A cap may be symmetric about an axis extending in a radial direction with respect to a central axis of the cap. A cap may be asymmetric about an axis extending in a radial direction with respect to a central axis of the cap. A cap may include an angled partition about a lens that is configured to direct phase-separated purging fluid delivered to the lens, by directing a gas phase of purging fluid in a substantially distal direction away from the lens and by directing a liquid phase of the purging fluid in a substantially radial direction away from the lens. A cap may further comprise a transparent lens. A cap may further comprise a second transparent lens to create a double paned insulating effect. A transparent lens may have a coating. A coating of a transparent lens may be a hydrophobic coating, an antireflective coating, or both. A cap may be coupled to an endoscope using at least one of an elastomeric sleeve providing a friction fit, a heat shrink sleeve, or one or more deflecting tabs. A purging fluid supply mechanism may be affixed to the endoscope using a heat shrink sleeve, the sleeve including circuitry disposed at least partially along the sleeve to provide a self-shrinking heat effect to the sleeve. An outer diameter of a cap may be provided with one or more scalloped features. A system may include a working channel seal for providing a substantially fluid-tight seal in an area around the working channel of the endoscope. A lens clearing flow field adjustment mechanism may be a nozzle provided in a cap. A lens clearing flow field adjustment mechanism may receive a purging fluid from a purging fluid supply mechanism integrated with an endoscope, modify a flow field of the purging fluid, and direct the flow field towards a lens. A cap may partially surround a lumen in a cap in which the endoscope is provided. A cap may fully surround a lumen in the cap in which an endoscope is provided. A cap may include a spatter deflection nozzle provided in the cap for deflecting spatter away from a lens. A system may include a flow deflection guide configured to redirect a flow field of the purging fluid delivered from the lens clearing flow field adjustment mechanism. A purging fluid may be carbon dioxide, dry air, oxygen, or nitrogen. A system may include a purging fluid supply mechanism external to the endoscope for supplying a purging fluid to a cap. A purging fluid supply mechanism may be an outer lumen of a multilumen sheath, wherein an endoscope is provided in an inner lumen of the multilumen sheath and a purging fluid is supplied to a cap via the outer lumen. A purging fluid supply mechanism may be a separate lumen affixed to an endoscope. A purging fluid supply mechanism may be a lumen extending from a cap substantially parallel to a longitudinal axis of the cap. A purging fluid supply mechanism may be affixed to an endoscope using one or more of a rubber cuff providing a friction fit, a heat shrink sleeve, or one or more deflecting tabs or clips.

Embodiments of a visualization system may include an endoscope having a lens and a working channel for a tool. A cap may surround a lens. A lens clearing nozzle may be provided in a cap for delivering purging fluid to a lens, wherein the cap is sized and configured to reduce entrainment of moisture in the vicinity of the lens. A purging fluid supply mechanism may be external to an endoscope for supplying a purging fluid to a cap. A lens clearing nozzle may be configured to deliver an angled jet of purging fluid to a lens. A purging fluid supply mechanism may be an outer lumen of a multilumen sheath, wherein an endoscope is provided in an inner lumen of the multilumen sheath and a purging fluid is supplied to a lens clearing nozzle via the outer lumen. A purging fluid supply mechanism may be a separate lumen affixed to an endoscope. A purging fluid supply mechanism may be affixed to an endoscope using one or more of a rubber cuff providing a friction fit, a heat shrink sleeve, or one or more deflecting tabs or clips. An outer lumen of a multilumen sheath may include a flow transition area for changing a flow pattern of a purging fluid in the vicinity of a cap. A system may include a working channel seal for providing a substantially fluid-tight seal in an area around a working channel of an endoscope. A system may include one or more guides for deflecting a purging fluid away from a working channel of an endoscope. A cap may include an opening in the cap opposite a lens clearing nozzle. An opening in a cap may be a lumen extending distally from the cap substantially parallel to a longitudinal axis of the cap. A guide may have a scooped shape that follows a contour around a portion of a perimeter of a cap. A guide may have an upper distal edge that is slanted at about 60 degrees proximally from a radial axis of the cap.

Embodiments of a visualization system may include an endoscope having a lens and a working channel for a tool. A system may include a cap surrounding a lens and a lens clearing flow field adjustment mechanism provided in the cap for delivering purging fluid to the lens. A system may include a heating element for heating either or both of an endoscope and a purging fluid such that condensation on a lens is reduced as compared to supplying the purging fluid without a heating element. A lens clearing flow field adjustment mechanism may be one or more nozzles configured to deliver an angled jet of the purging fluid to a lens. A purging fluid may be supplied to a cap through a supply tube having a wall with embedded filars. A heating element may be a wound heating element around the supply tube that provides energy through the embedded filars. A heating element may be configured to heat an endoscope. One or more sensors and a power supply may be in communication with a heating element, whereby the sensors provide feedback to the power supply to control power to the heating element. One or more thermal interface materials may reduce thermal impedance between a heating element and one or both of a lens and a supply line for supplying a purging fluid to a cap. A cap may be configured to thermally insulate a heating element from a patient to maintain a safe exposure temperature on an external surface of the heating element.

Embodiments of a visualization system may include an endoscope having a lens and an external working channel around the endoscope configured to receive a catheter. An external working channel may comprise at least one of a sealed air channel or a vacuum gap that provides thermal insulation, and a distal sealing feature configured to limit contaminant access to the external working channel. A system may include a cap surrounding a lens and a lens clearing nozzle provided in the cap for delivering an angled jet of purging fluid to the lens, wherein the cap is sized and configured to reduce entrainment of moisture in the vicinity of the lens. An external working channel may be provided in a multilumen sheath that fits over an endoscope. An external working channel may be affixed to an endoscope using at least one of a heat shrink sleeve or one or more deflecting tabs or clips. An external working channel may include evacuated lumens separated by thin ribs.

Embodiments of a visualization system may include an endoscope having a lens, a cap at least partially covering the endoscope, and a heating sheath or wrap. A heating sheath or wrap may provide one or more of: direct heating of an outer diameter of the endoscope or a face of the endoscope, or indirect heating by integration with the cap.

Embodiments of a visualization system may include an endoscope having a lens, a catheter, and a flexible catheter vacuum jacket for reducing one or more of convection, conduction, or radiation to an external surface of the catheter.

Embodiments of a visualization system may include an endoscope having a lens and a heating element for heating either or both of the endoscope and a purging fluid such that condensation on the lens is reduced. A heating element may be configured to be used in conjunction with a cap or shroud providing heated or room temperature purging fluid to a lens. A cap or shroud may provide external insulation to the heating element. An endoscope may be a bronchoscope and the system may further comprise a cryospray catheter as the tool to be used through the working channel of the bronchoscope.

Other embodiments are also described and claimed.

BRIEF OVERVIEW OF THE DRAWINGS

FIGS. 3A-3C depict various views of a visualization system including a cap, a flow transition sheath, and a purging fluid supply mechanism according to an embodiment of the present disclosure.

FIGS. 19A-19E depict a cap according to an embodiment of the present disclosure.

FIGS. 21A-21C depicts a cap according to a further embodiment of the present disclosure.

FIGS. 22A-22B depict a cap and clip according to an embodiment of the present disclosure.

DETAILED DESCRIPTION

Figure 1A:
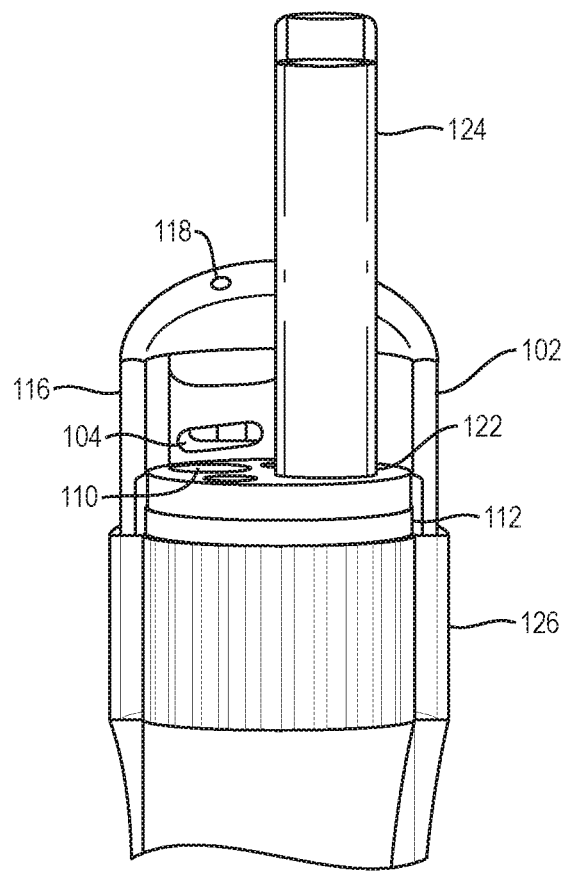
FIGS. 1A-1B depict a visualization system employing a cap, a sleeve, and a purging fluid supply mechanism according to an embodiment of the present disclosure.

Various embodiments, described here or otherwise, within the scope of the present disclosure include a visualization system. The systems include a lens clearing flow field adjustment mechanism that provides a flow field to purge moisture from the space adjacent to the lens of an endoscope. The systems incorporate a shroud and/or cap attachment for the endoscope that minimizes moist fluid entrainment and also may deflect incoming particles or bodily fluids. The term "lens" is to be understood as including an optical device as part of an image capture device of a distal end of an endoscope (such as one or a series of lenses that may be arranged along a common axis or a CCD) and/or a transparent protective cover or screen for the optical device.

In some embodiments, a purging fluid, such as a gas, is introduced to a lens from a lens clearing flow field adjustment mechanism, such as a nozzle, to clear particles or fluids from the lens cover. The mechanisms, such as nozzles, may be configured in different ways to modify and direct the flow field of the purging fluid. In some embodiments, a secondary nozzle is directed such that incoming particles and fluids may be deflected away from the lens assembly. In further embodiments, purging fluid as a gas may be supplied through a rinse channel of the endoscope, and a cap may modify, direct, detect or cycle the flow of the gas in order to improve the lens clearing effect, drain liquids from the cap (sometimes via a phase separator mechanism), and/or deflect gases longitudinally away from the lens cover to provide a gas buffer or barrier.

Various embodiments may also incorporate a heating element to provide purging fluid at body temperature or a slightly elevated temperature. Providing heating to the endoscope tip is needed to avoid condensation and freezing of condensates and bodily fluids in contact with the lens, a condition unique to cryotherapy procedures, particularly cryospray techniques. In addition, and not unique to cryotherapy, heating the endoscope tip may prevent condensation by keeping the lens above an ambient dew point temperature. Other embodiments may incorporate an electrical heating element, e.g., within a sleeve that connects the distal shroud or cap to the endoscope. In some cases, sensors and a power supply may be included to provide feedback-controlled temperature regulation of the endoscope tip.

Exemplary embodiments of the visualization systems may be particularly well suited to applications involving endoscopic cryotherapy procedures, especially spray cryotherapy. Each of these aspects and advantages are described in more detail below.

Visualization Systems

In various embodiments, a visualization system includes a distal cap with a lens clearing flow field adjustment mechanism. The mechanism may include one or more nozzles for creating and adjusting a flow field. Some nozzles may be configured to deliver an angled jet of purging fluid to the lens at the distal end of an endoscope to which the cap is attached, such as a gaseous nitrogen, dry air, oxygen, or carbon dioxide jet. The purging fluid and nozzles may be configured within the cap in various ways to prevent condensation on the lens by purging moisture from the gas surrounding the lens cover, clearing liquids from the lens cover, and hydrodynamically deflecting incoming spatter, particulates, and fog.

Figure 1B:
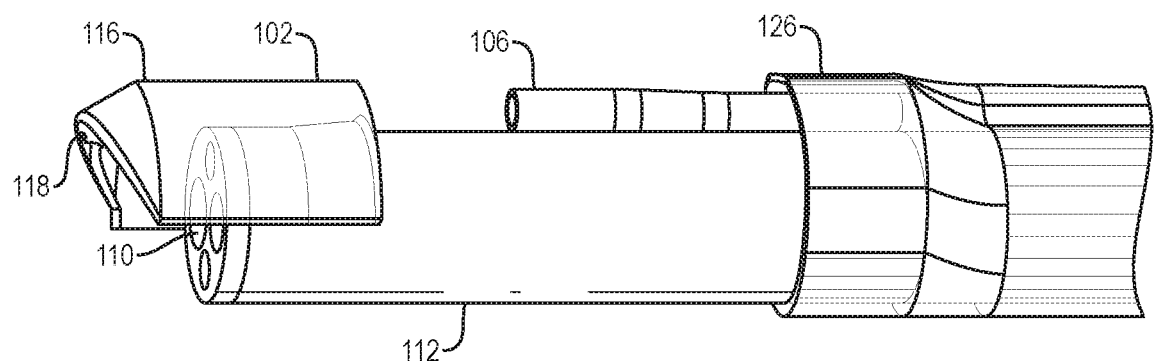
Figure 2C:
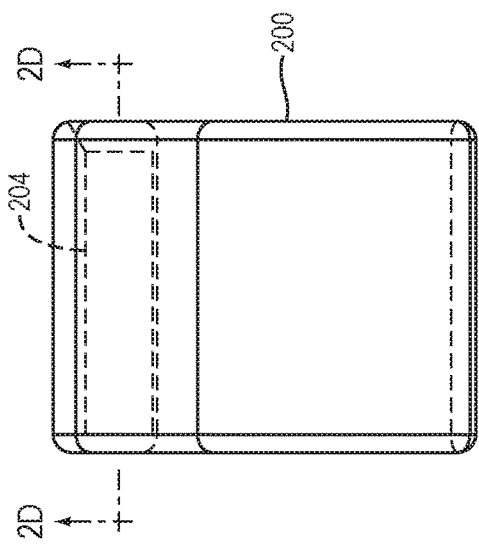
FIGS. 2A-2D depict various views of a clip according to an embodiment of the present disclosure.
Figure 2D:
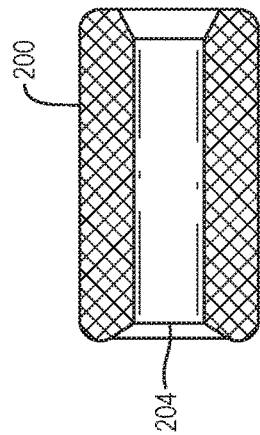
Figure 2B:
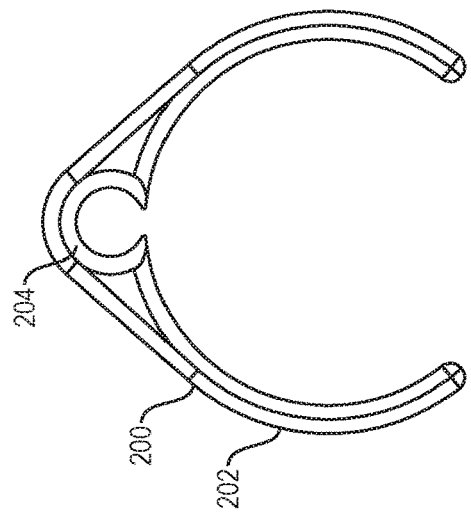
Figure 2A:
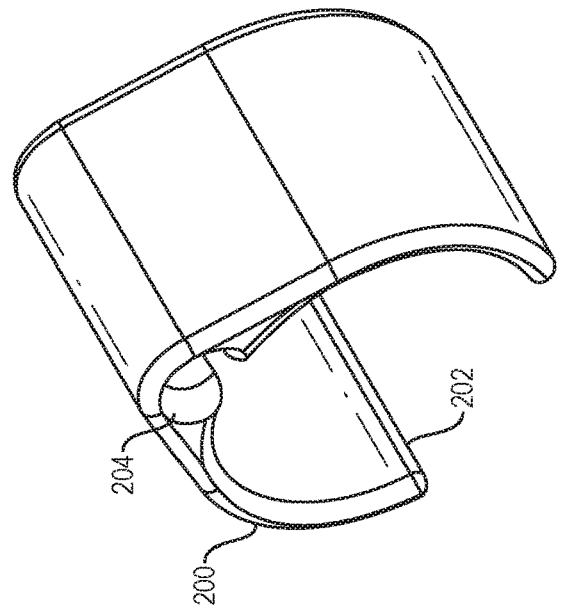
Figure 4C:
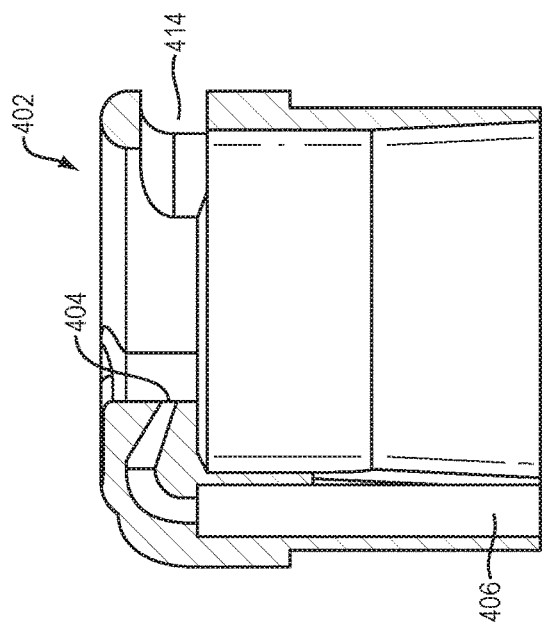
FIGS. 4A-4D depict various views of a cap according to an embodiment of the present disclosure.
Figure 4D:
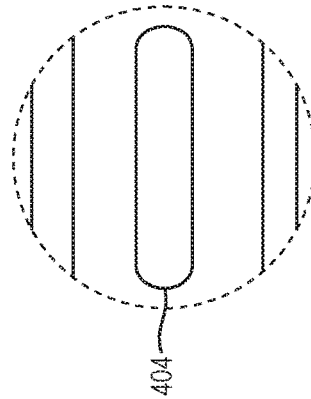
Figure 4B:
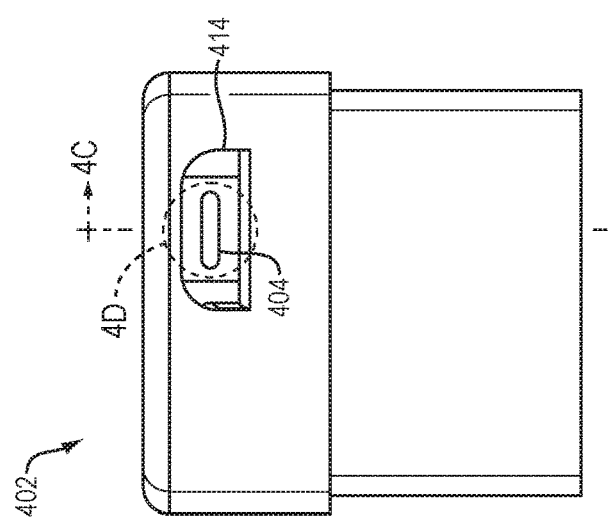
Figure 4A:
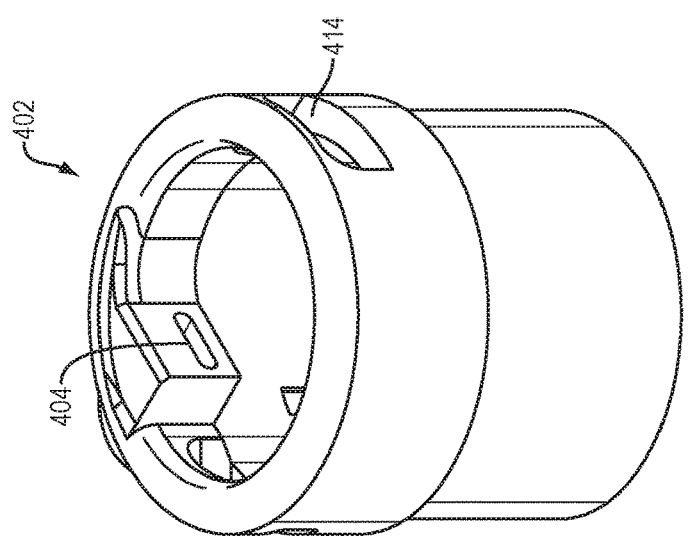
Figure 5C:
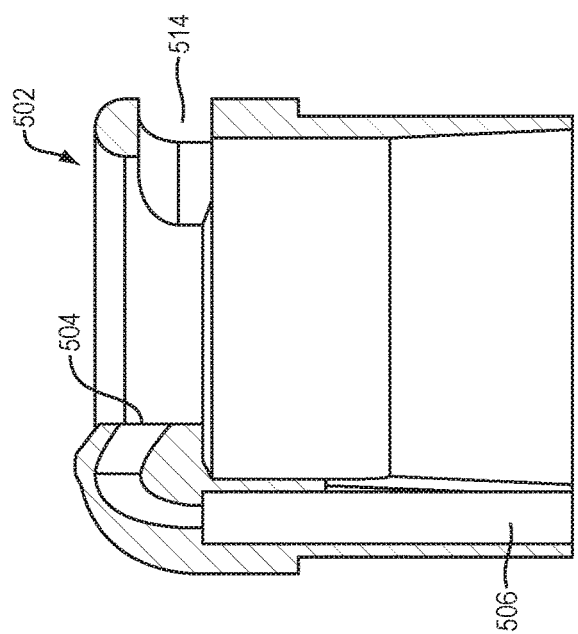
FIGS. 5A-5D depict various views of a cap according to another embodiment of the present disclosure.
Figure 5D:
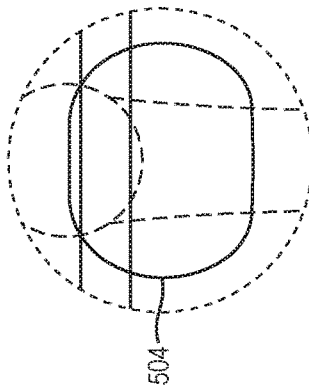
Figure 5B:
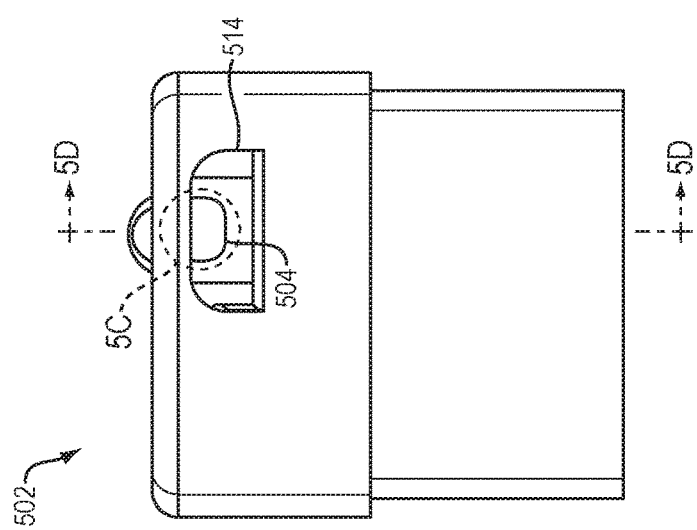
Figure 5A:
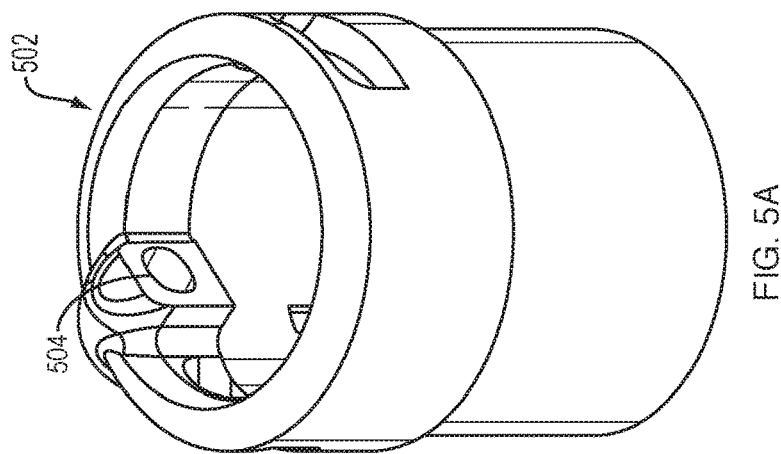

Embodiments of a distal cap attachments may take several forms. For example, FIGS. 1A and 1B depict a distal cap 102 that is asymmetric about an axis extending in a radial direction with respect to a central axis of the cap. The cap is connected to a heat shrink or friction sleeve 126 surrounding an endoscope 112 in which the shrouding portion 116 surrounds only a part of the distal portion of a catheter 124 and/or endoscope 112. Asymmetry serves among other purposes to minimize blocking of the gas egress area across the lens 110 and distal end of the endoscope 112 and reduces a profile of the cap 102 from blocking the flow of the purging fluid. Purging fluid as a gas may vent to a side of a patient's body around the outside of the endoscope 112.

FIG. 1A depicts a cap 102 with a lens clearing flow field adjustment mechanism that includes two nozzles: a lens clearing nozzle 104 directed towards the lens cover 110 of endoscope 112, and a spatter deflection nozzle 118 directed out and away from the lens 110 at an angle with respect to a central axis of the cap, for deflecting incoming spatter, particulates, and fog. There may be benefits for any range of angles from a 0° angle (pointing distally and substantially aligned with the central axis of the cap) to an angle capturing the line of sight between nozzle 118 and the edge of scope 112. FIG. 1A depicts nozzle 118 oriented at an angle of approximately 135° from the central axis of the cap 102, such that spatter is barely diverted from impacting the scope. A visualization system may utilize zero or more lens clearing nozzles 104 and zero or more spatter deflection nozzles 118, depending on the particular application. Working channel 122 allows a tool, such as a cryosurgery tool, to be deployed via catheter 124 to the vicinity of the visualization system.

FIG. 1B illustrates the cap 102 in position at the distal end of the endoscope 112, but disconnected from the sleeve 126. Purging fluid supply mechanism 106, which is a single lumen supply tube or line along the length of the endoscope 112 in this embodiment, provides a channel to the endoscope tip via the cap 102 for purging fluid. The purging fluid supply mechanism 106 is in fluid communication with a fluid such as a gas, which may be room temperature or heated. Purging fluid supply mechanism 106 is disposed within a lumen of the sleeve 126 along the endoscope 112.

In some embodiments, a spatter deflection nozzle and a lens clearing nozzle are both provided with a purging fluid via a purging fluid supply mechanism (e.g., a single lumen feed tube in FIG. 1B) connected to a distal cap, e.g. cap 102, as shown in FIGS. 1A and 1B. The purging fluid supply mechanism may be secured to the endoscope at one or more points using clips. An exemplary clip 200 suitable for this purpose is depicted in FIGS. 2A-2D. As shown, clip 200 includes a first C-shaped portion 202 to accept and clip onto an endoscope 112. The clip 200 may include a second C-shaped portion 204 to accept and clip onto purging fluid supply mechanism 106. One or more clips may be used to run a purging fluid supply mechanism along the length of the endoscope.

A cap and/or purging fluid supply mechanism may be connected to an endoscope in a number of ways. For example, these elements may be connected to an endoscope via a heat shrink connection sleeve. In some embodiments, a circuit and battery may be integrated into the visualization system, allowing in some embodiments a heat shrink connection sleeve to generate its own heat to in effect, self-shrink. Alternatively, or in addition, the heat shrink sleeve may be externally heated with a heat gun. In other embodiments for connecting a cap and/or a purging fluid supply mechanism to the endoscope, a tube and rubber roll-on cuff, sleeve, deflecting tabs, membrane for a friction fit, or the like, may be employed. A cap and/or delivery sheath may be extruded or molded from PVC, Pebax 6333, or similar material.

In the example of FIGS. 3A-3C, a purging fluid supply mechanism 306 is formed by annular extrusion in a sheath covering the endoscope. The purging fluid supply mechanism may be formed as a multilumen extrusion in which the endoscope slides into a cylindrical sleeve that provides the purging fluid (e.g., purging fluid supply mechanism 306 and endoscope 312 in FIGS. 3A-3C), or as a single lumen extrusion in which the purging fluid supply mechanism is attached to the system using a sleeve, one or more snap-fit clips (e.g., purging fluid supply mechanism 306, sleeve 126, and clips 200 in FIGS. 1A-2D), or some other means. Still further, any element of the visualization system may be designed as a temporary attachment means that is removed when the element or system is sterilized. A purging fluid supply mechanism may also be configured as an outer lumen of a multilumen sheath. The endoscope may slide into an inner lumen of the multilumen sheath, while the purging fluid is supplied to the cap via the outer lumen.

In various embodiments, a purging fluid for a system may be, for example, carbon dioxide ($CO_2$), nitrogen ($N_2$), dry air, or oxygen ($O_2$). The purging fluid may be supplied in a number of ways. In one embodiment, the fluid supply mechanism is a line and may connect directly to a console, such as a cryosurgery console as described in connection with FIGS. 9-11B, in which nitrogen is supplied to the supply line. In other embodiments, the fluid supply line may be connected to disposable canisters of purging fluid. The purging fluid may also be supplied via an insufflator unit, or commercial compressed gas bottles with a regulator and valve. A mass flow or other suitable controller may be used to regulate and/or vary a flow rate of purging fluid during operation. Pressure feedback from the supply line or taken from within a body lumen, or both, may be utilized to reduce a risk of distension or pneumothorax.

A purging fluid may be supplied continuously to the nozzles or other lens clearing flow field adjustment mechanisms of the visualization system, or a fluid supply may be valved or metered so that the purging fluid flows on an as-needed basis. In some embodiments, a button or switch may be provided that allows the flow of the purging fluid to be temporarily increased, in order to perform touch-up jobs or provide a bolus of purging fluid in the event that visualization becomes impaired despite the normal operation of the visualization system.

In some embodiments, the distal cap may be symmetrical about an axis extending in a radial direction with respect to a central axis of the cap, such that the cap has a substantially uniform profile circumference. By making the cap symmetrical, for example, a sheath or sleeve around the scope can function to both secure the cap and deliver purging fluid to the lens clearing flow field adjustment mechanism. For example, referring to FIGS. 3A-3C, an embodiment of a system includes distal cap 302 with a substantially uniform profile circumference 316 at the distal end of the cap 302. Purging fluid supply mechanism 306 delivers purging fluid to the lens clearing flow field adjustment mechanism, in this case nozzles 304 (and/or an additional spatter deflection nozzle(s)) on the distal end of the cap 302. The purging fluid supply mechanism 306 includes channels that fluidly communicate with the channels of a flow transition sheath 318 that is circumferentially mounted on the endoscope 312.

The channels of a flow transition sheath may vary in cross-sectional width and shape along the length of the sheath. Variable cross-sections may be used to increase or decrease the mass flow rate of the fluid being supplied from the purging fluid supply mechanism, through the flow transition sheath, and to the cap. A cap may include one or more nozzles (e.g., a pair of nozzles 304 in FIGS. 3A-3C) that are in fluid communication with the flow transition sheath and/or the purging fluid supply mechanism. Nozzles may be angled towards and across the lens and ultimately towards a drain. For example, in FIGS. 3A-3C, drain 314 is a gap, hole, or aperture in the cap 302 that ensures the purging fluid does not build-up at the distal end of the cap 302 within the profile circumference 316. The drain 314 allows for purging fluid to clear from the cap 302 and lens 310. Guides 308 extend from the cap 302 in proximity to the nozzles 304 in order to direct flow towards the lens 310 and drain 314 and away from catheter 324. The guides 308 extend only near or up to a tangential portion of the lens 310 such that they do not block the line of vision from the lens 310 to the catheter 324 extending from a working channel of the endoscope 312.

A working channel seal, e.g., seal 322 of FIG. 3B, may be used to create a substantially fluid-tight seal for a catheter or other tool within the working channel such that fluids may be minimized or eliminated from entering the working channel of the endoscope.

In various embodiments, the lens clearing nozzle, as an example of the flow field adjustment mechanism for the purging fluid, may be dimensioned, shaped, or positioned, with respect to the lens, to accomplish the desired flow field and lens clearing effect. For example, referring to FIGS. 4A-4D, an embodiment of a system includes cap 402 with a nozzle 404 that is directed generally across the cap 402 and towards a drain 414. The drain may vary in dimensions according to the particular application and desired flow, purge, or drain effects, among other effects, including, in this example, 4 mm by 1 mm. The nozzle 404 is supplied with purging fluid from the purging fluid supply mechanism 406 that is a channel within a wall of the cap 402. The nozzle 404 transitions from a wider cross-section to a narrower cross-section and is angled steeply downwards and towards the inside of the cap 402, where the lens is located once the cap 402 is mounted onto an endoscope. This allows for a narrow and aggressive flow of purging fluid across the endoscope lens cover.

Nozzle angles for this and other embodiments may be determined depending on the application and desired flow, purge, or drain, effects, among other effects, by using, for example, computational fluid dynamics (CFD) simulation. A range of suitable nozzle angles may be less than 180° (180° being direct impingement on the lens with reference to a 0° angle being distal to and substantially aligned with the central axis of the cap) to about 90° (nearly parallel to the lens).

As another example, referring to FIGS. 5A-5D, cap 502 is shown with a nozzle 504 that is directed generally across the cap 502 and towards drain 514. A cross section of drain 514 is similar to drain 414. The nozzle 504 is supplied with purging fluid from the purging fluid supply mechanism 506 that is a channel within a wall of the cap 502. The nozzle 504 here transitions from a narrower cross-section to a wider cross-section and is angled less steeply downwards, compared to the nozzle of FIGS. 4A-4D, towards the inside of the cap 502 and the lens, once the cap 502 is mounted onto an endoscope. This allows for a wide and gentle flow of purging fluid across an endoscope.

The cross-section, transitional geometries, and angles used for this and other embodiments may be application specific and may depend on various dimensional requirements and/or desired flow, purge, drain, or deflection effects, among other effects, e.g., referring to FIGS. 5A-5D, dependent on endoscope size and the diameter of the purging fluid supply mechanism 506 in order to cover the diameter of the lens cover.

A profile of the lens clearing flow field adjustment mechanism, such as a lens clearing nozzle and/or a spatter deflection nozzle (as described in FIGS. 4D and 5D) may vary depending on the application. For example, the cap of FIGS. 4A-4D has a substantially elliptical nozzle, whereas the cap of FIGS. 5A-5D has a substantially round nozzle. Other nozzle profiles (e.g., slot, square, triangular, a combination of shapes, etc.) may be employed. In addition to varying the profile of the nozzles, other parameters may be varied as well. Examples of parameters that may be adjusted depending on the application include the angle of the nozzles, the number of nozzles, and the flow rate of the purging fluid through the nozzles.

Figure 6A:
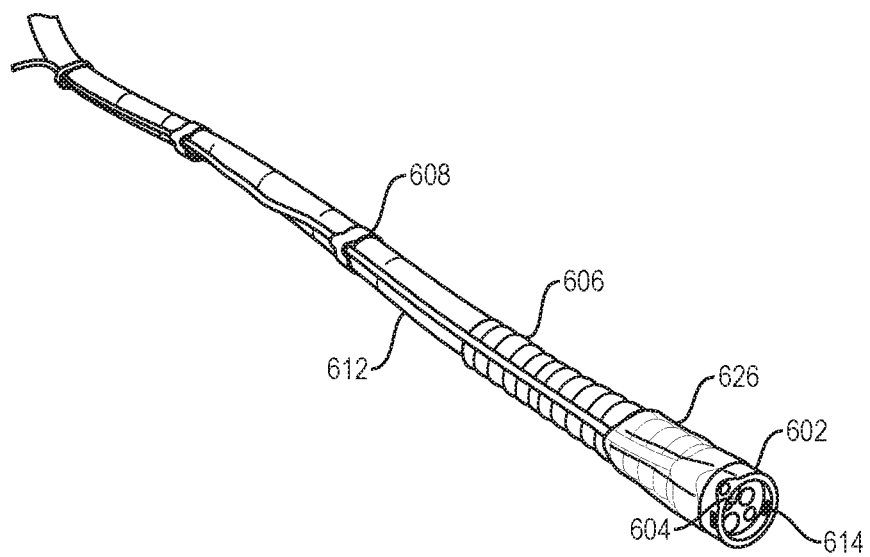
FIGS. 6A-6C depict various views of an assembled visualization system according to embodiments of the present disclosure.
Figure 6B:
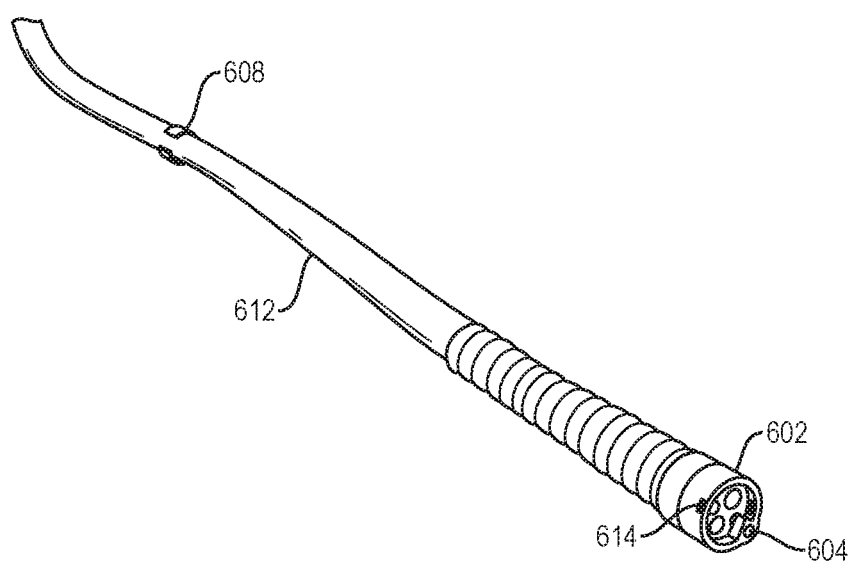
Figure 6C:
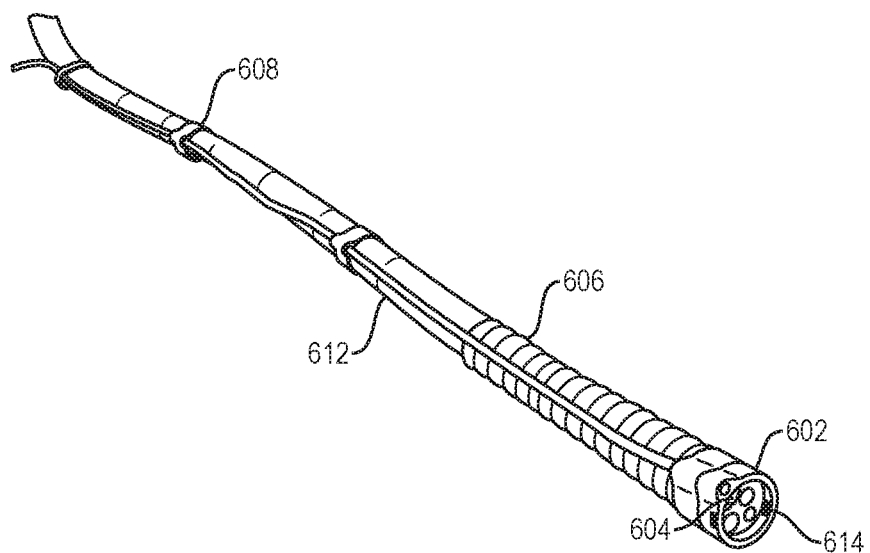

As a further example, FIGS. 6A-6C provide various views of an assembled visualization system with a cap 602 similar in design to the cap 502 depicted in FIGS. 5A-5D. The cap 602 includes nozzle 604 and drain 614. The cap 602 is connected to the endoscope 612 by a sleeve 626, and supplied with purging fluid by a purging fluid supply mechanism 606. The purging fluid supply mechanism 606 is disposed along the endoscope 612 and secured to the scope through the use of one or more clips 608, which may be similar in configuration to that of clip 200 in FIG. 2A-2D.

In various embodiments, the cap may comprise materials, dimensions, and features to facilitate secure attachment to the scope. For example, referring to FIGS. 19A-21C, the base of the cap may be an elastic cuff (see, e.g., 1918, 2018, and 2118 in FIGS. 19A-21C), such as a thermoplastic elastomer (TPE) material. An elastic cuff may provide a friction fit component that interfaces with the endoscope outer diameter. Ribs may be included inside the cuff and sized and configured to meet a desired or required friction range for ease of insertion/removal onto and off of a range of endoscope outer diameters. Cuffs may be overmolded or made as a separate part and bonded to a transparent substrate. The bottom edge (proximal) of a cuff may be tapered to guide the endoscope into position during attachment at the cap. An outer profile of the cuff may be undersized so that when stretched over an endoscope, it expands to provide a straight/smooth outer profile.

Figure 19B:
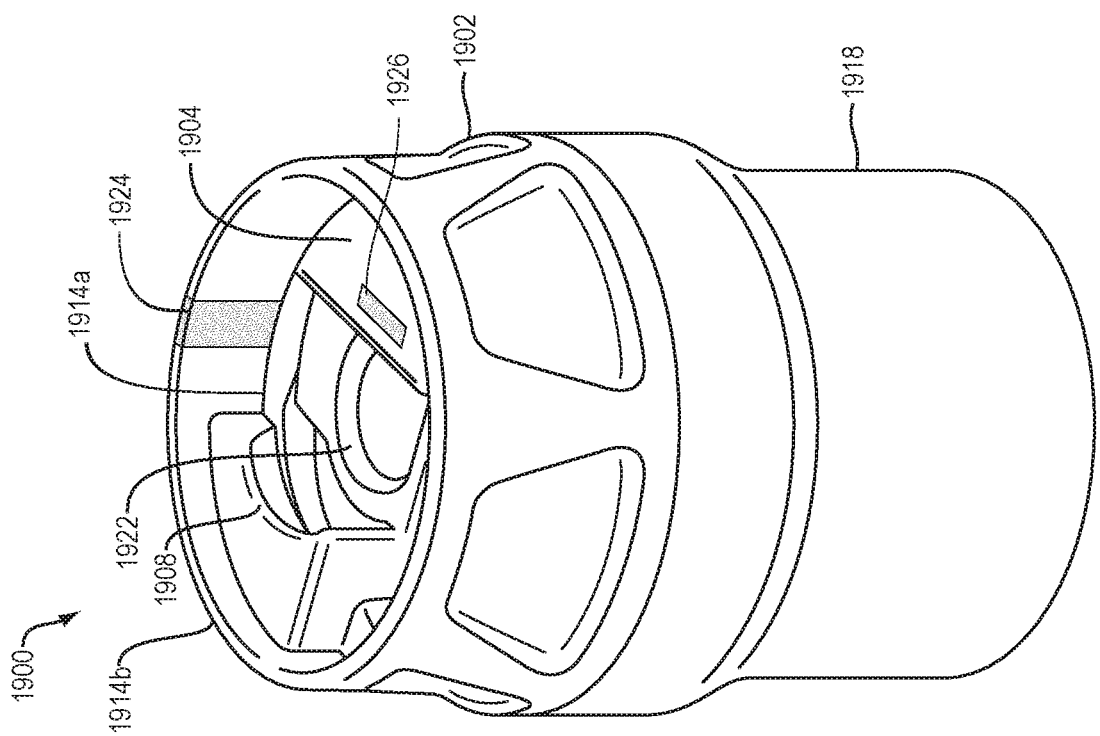
Figure 19C:
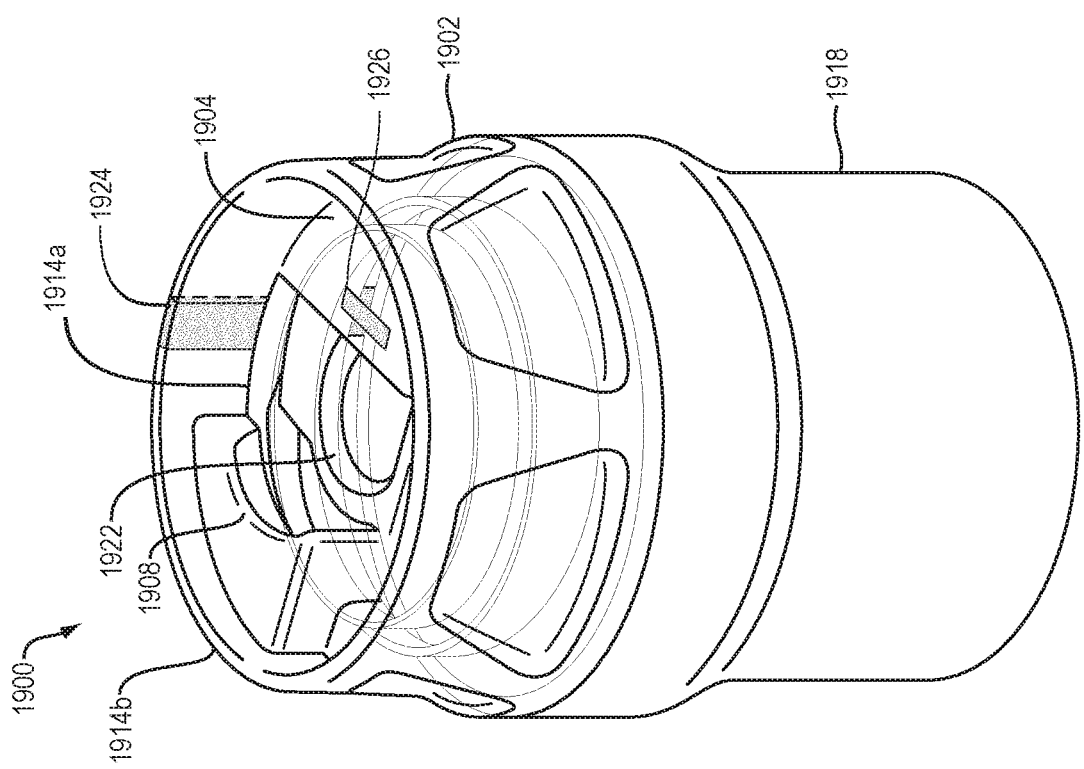
Figure 19E:
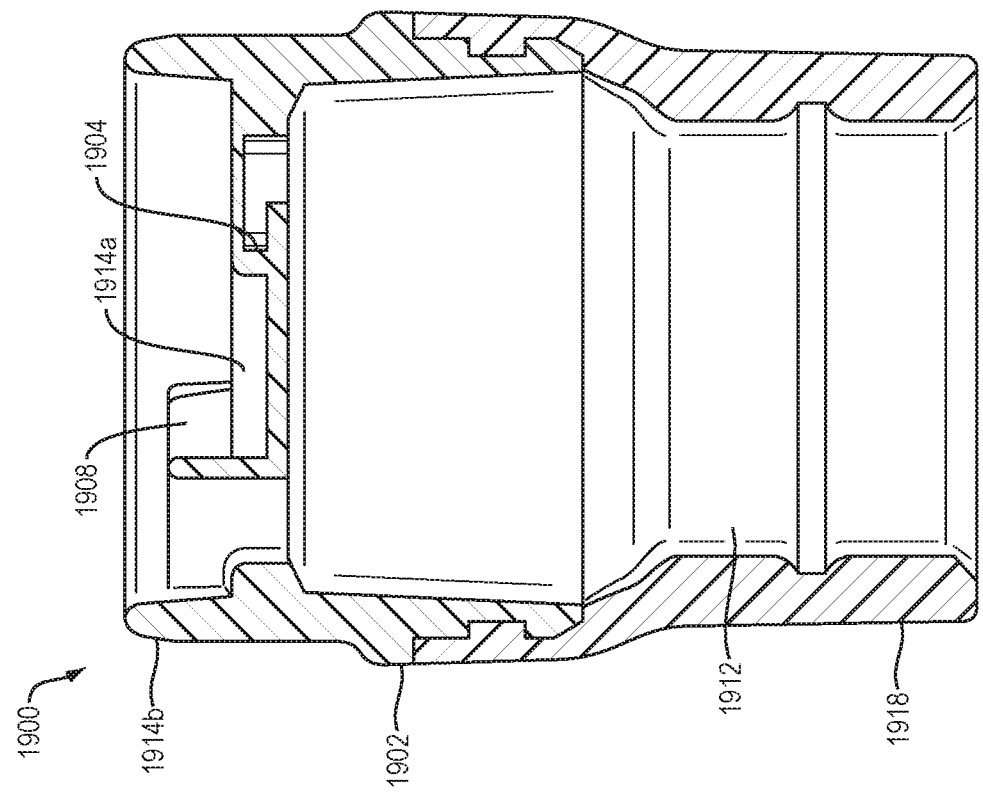
Figure 20A:
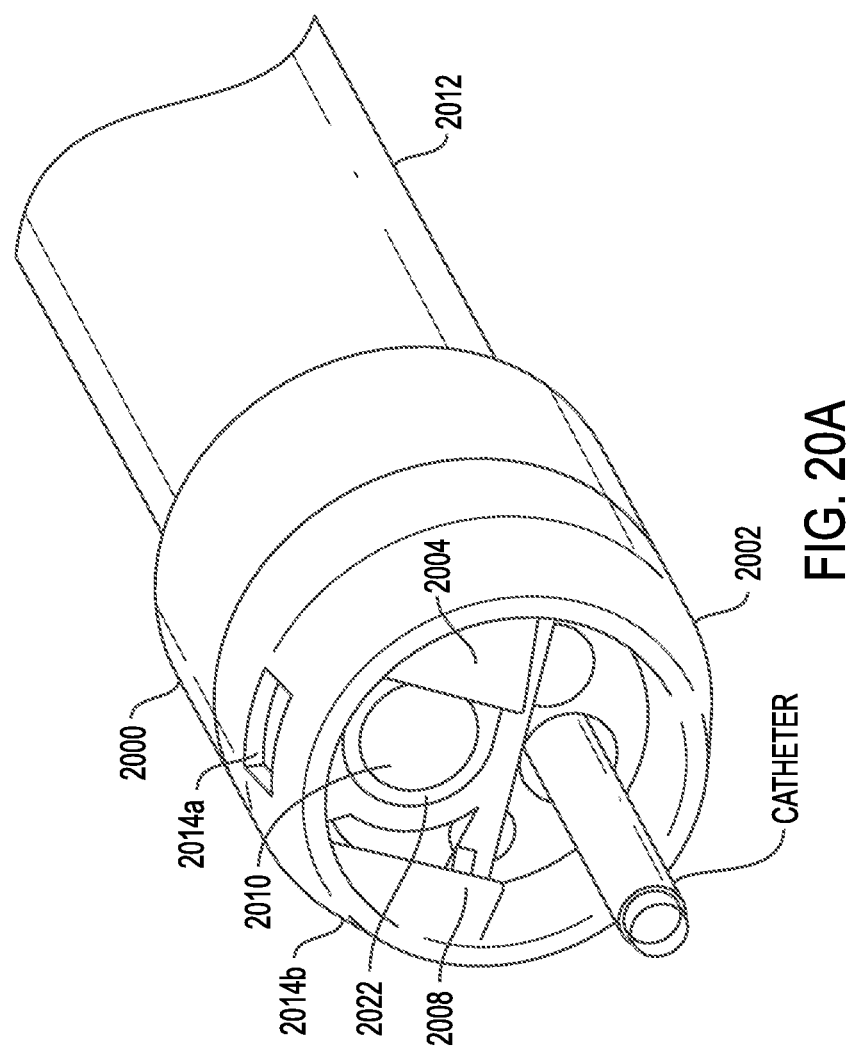
FIGS. 20A-20C depict a cap according to another embodiment of the present disclosure.
Figure 20C:
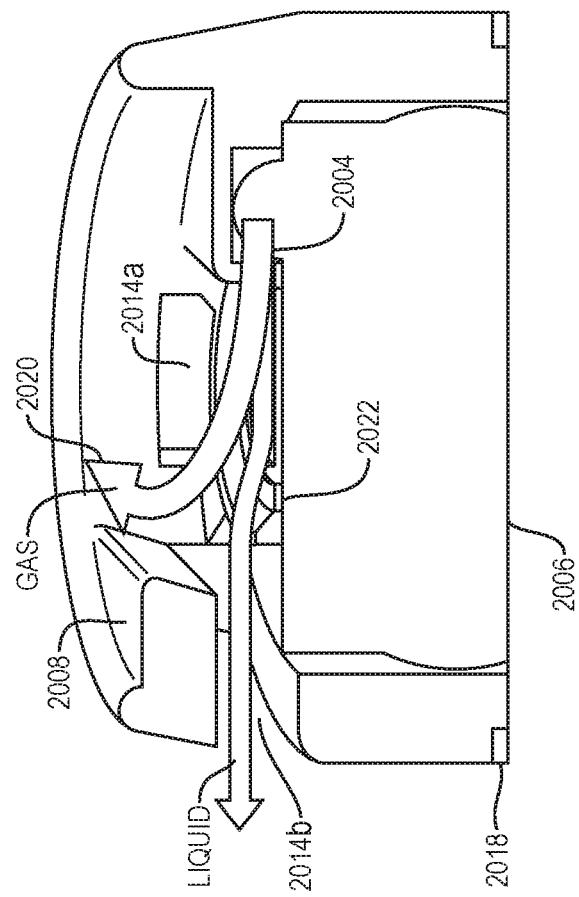
Figure 20B:
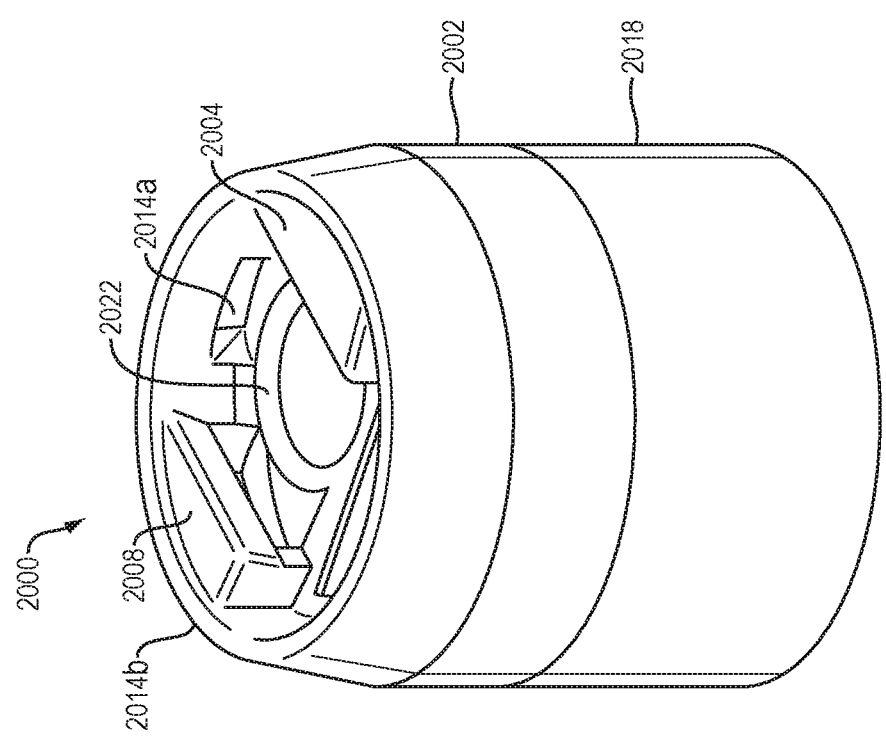

In each of FIGS. 19A, 20A, and 21A, a cap according to embodiments of the present disclosure is depicted (e.g., 1900, 2000, and 2100, respectively) with a tapered rigid plastic region (1902, 2002, and 2102) and an elastic cuff region (1918, 2018, and 2118). The tapered rigid plastic region has an outer diameter that is tapered, for example, at about 15 degrees. The cap is mounted onto an endoscope (1912, 2012, and 2112) through the frictional grip of the cuff around an end region of the endoscope. Tapering and scalloping is provided on the tapered rigid plastic region to help the user handle and fit the cap in the right position relative to the endoscope face features.

In this and other embodiments, scalloping and tapering on the distal cap may be adjusted according to preference and the circumferential distal edge of the tapered rigid plastic region (e.g., 1902, 2002, and 2102) may be fully rounded with the distal profile tapered to provide smooth, atraumatic insertion in the patient.

In various embodiments, a distal cap may be configured to receive purging fluid from within the endoscope, and/or the cap may include a flow deflection guide structure to direct purging fluid. For example, referring to FIGS. 19A-19E, an embodiment of a visualization system includes a cap 1900 with a lens clearing flow field adjustment mechanism, which is a nozzle 1904. The nozzle 1904 receives a purging fluid from a purging fluid supply mechanism, which is a channel in the endoscope 1912. The nozzle 1904 directs the purging fluid towards the lens 1910 of the endoscope 1912.

The cap 1900 also includes a guide 1908 that directs the flow of the purging fluid after it has traveled from the nozzle 1904 and across the lens 1910.

Figure 19D:
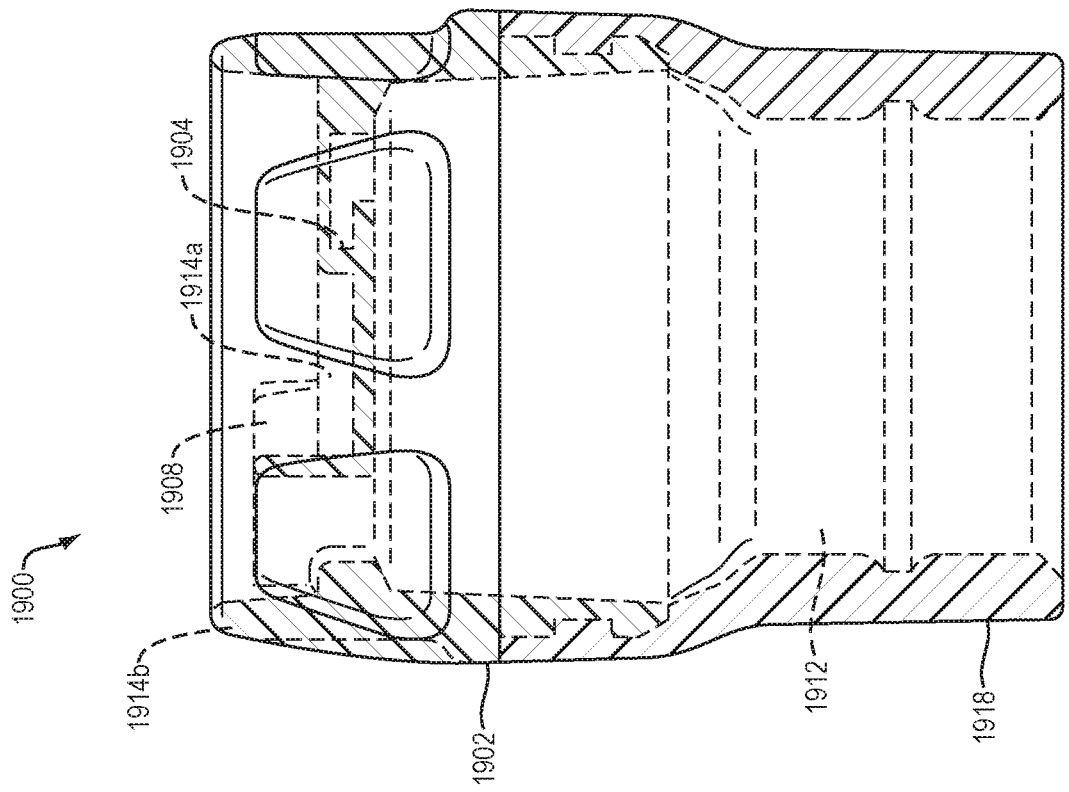

The guide 1908 is curved and angled toward a first drain 1914a, but may be configured differently depending on the desired flow deflection path for the purging fluid. The guide 1908 is curved and angled to guide the purging fluid generally in a distal direction with an angle of, for example, about 60° proximally from a radial axis of the cap. The guide 1908 may also deflect or recycle the fluid generally around the inside rim of the cap 1902. With gas as a purging fluid, this path can act to create a vortex in front of the cap as the gas circles distally beyond the endoscope tip 1912. The guide 1908 has a C-shaped notch that allows for better visibility from the lens 1910. The purging fluid exits from over the lens 1910 to outside of the cap 1900, clearing the area around the lens 1910 for additional purging fluid from the nozzle 1904. A partition 1922 prevents fluids that may accumulate beneath the guide 1908 from reaching the lens 1910. The partition 1922 may also deflect the purging fluid from the nozzle 1904 to the guide 1908 while liquids are disposed of via the drain 1914b. This includes partition 1922 acting as a "phase separator", e.g., by directing phase-separated purging fluid delivered to the lens, by directing a gas phase of purging fluid in a substantially distal direction away from the lens and by directing a liquid phase of the purging fluid in a substantially radial direction away from the lens. Referring to FIGS. 19B and 19D, the cap may be optically transparent so as not to interfere with visibility.

In these and other embodiments, portions of the cap may be made of a transparent material to improve visibility. Markings may also be included on the cap to assist in properly attaching the cap to a scope. For example, in FIG. 19B, the tapered rigid plastic region 1902 of the cap 1900 may be made of a transparent material, such as Lexan, so that there is a clear line of vision from the lens 1910 to the target site through the tapered rigid plastic region 1902. Conspicuous markings 1924 and 1926 may be printed or otherwise disposed onto the cap 1900, such as on the plastic region 1902 and the cuff region 1918. The marking 1924 is an alignment marking that assists the user in placing the cap 1900 onto the endoscope 1912 such that the cap 1900 and all of its features are properly aligned with the lens 1910 and working channel, and not rotationally out of position. The marking 1924 extends across the drain 1914a and onto the cuff 1918. A user may align the marking 1924 such that it is centered with respect to the lens 1910. Additionally, the marking 1926 is disposed on the guide 1908. The marking 1926 is positioned perpendicular to a radius of the lens 1910 and is at a distance from the circumference of the lens 1910 such that when the cap 1900 is properly mounted onto the endoscope 1912, an image viewed through the lens 1910 does not have any portion of the marking 1926 within the field of vision. If the cap 1900 is not properly secured to the endoscope 1912, at least a portion of the marking 1926 may be viewable through the lens 1910. This may indicate that the cap 1900 needs to be further pressed onto the distal end of the endoscope 1912 for a secure fit. Markings may be added to a cap via methods such as, e.g., pad printing, laser printing, or laser etching.

Various embodiments, of a system within the scope of the present disclosure include a nozzle as a lens clearing flow field adjustment mechanism on the cap that is directed toward a lens of an endoscope, one or more guide members, and one or more drains. For example, referring to FIGS. 20A-20C, cap 2000 is shown with a lens clearing nozzle 2004. The nozzle 2004 delivers a purging fluid from a purging fluid supply mechanism, which is a channel in the endoscope. The nozzle 2004 directs the purging fluid towards the lens 2010 of endoscope 2012. The cap 2000 also includes a guide 2008 that directs the flow of the purging fluid after it has traveled from the nozzle 2004 and across the lens 2010. The guide 2008 has a wedge-shape that is both angled towards a first drain 2014a adjacent to the guide 2008 and a second drain 2014b that is below the guide 2008. The partition 2022 may act as a phase separator mechanism to drain liquids and/or deflect gases away from the lens cover 2010 to provide a gas buffer or barrier. The partition 2022 surrounding lens cover 2010 redirects the flow upward toward the guide 2008. Heavier liquids (e.g. as a liquid phase of the purging fluid) are unable to change direction quickly due to momentum, and so they exit through the second drain 2014b in a substantially radial direction away from the lens, while gases (e.g., as a gas phase of the purging fluid) are directed to guide 2008, which directs the gases in a substantially distal direction away from the lens. The guide 2008 may direct any gases away from the lens towards the first drain 2014a, as well as direct any gases distally away from the cap 2000. Any liquids from the purging fluid may be directed downward by the angled wedge of the guide 2008 towards the second drain 2014b, as well as directed toward the face of the endoscope 2012. The endoscope 2012 may have a channel that can receive the purging fluid via suction for venting and/or recycling of the purging fluid through the endoscope 2012. The second drain 2014b may incorporate, for example, a 90° (full quadrant) drain slot for the elimination of fluid accumulation. Purging fluid may egress from over the lens 2010 to outside of the cap 2000, clearing the area around the lens 2010 for additional flow of purging fluid from the nozzle 2004. The partition 2022 acts to minimize or prevent fluids that may accumulate beneath the guide 2008 from reaching the lens 2010.

In various embodiments, a cap may include a transparent lens that has a coating, and a lens clearing flow field adjustment mechanism, such as a nozzle, that may be created by a gap between the cap and the endoscope on which it is mounted. For example, FIGS. 21A-21C depict cap 2100 with lens clearing nozzle 2104. The nozzle 2104 delivers a purging fluid from purging fluid supply mechanism 2106, which is a channel surrounding the endoscope 2112 created by the cap 2100. The nozzle 2104 is created by a slant on an inner surface of the cap 2100 that narrows the gap of the purging fluid supply mechanism 2106 and directs the purging fluid towards the lens 2110 of endoscope 2112. A transparent lens 2122 may be inserted and installed through the drain 2114. With the transparent lens 2122 in position over the lens 2110, a small gap may be created between the distal surface of the lens and a proximal surface of a guide 2108. This gap created by the guide 2108 and the transparent lens 2122 directs the flow of the purging fluid after it has traveled from the nozzle 2104 and across the lens 2110. The guide 2108 may direct the fluid across the distal surface of the transparent lens 2122 and towards the drain 2114. The purging fluid may exit from over the lens 2110, between the guide 2108 and the transparent lens 2122, across the transparent lens 2122, and outside of the cap 2100, clearing the area around the lens 2110 for additional flow of purging fluid from the nozzle 2104. This configuration of the transparent lens may create a double paned insulating effect that further protects the lens, and may be incorporated in other embodiments. In various embodiments, a transparent lens may have a permanent hydrophobic and/or antireflective coating to allow universal operation with different endoscope types, brands, and sizes. A transparent lens may be glass, such as gorilla glass or borosilicate glass, or it may consist of highly polished polycarbonate. A cap may include a second transparent lens to create a double paned insulating effect.

In various embodiments, the system includes a catheter that is mounted to the endoscope using one or more clips. The cap on the endoscope includes a parallel extension through which the catheter is disposed. For example, referring to FIGS. 22A and 22B, cap 2202 is mounted at the distal portion of the endoscope 2212. The cap may be configured as in any of the embodiments described above, or as otherwise within the scope of the present disclosure. A catheter 2224 may be mounted to the endoscope 2212 by using one or more clips 2204. The clip 2204 has a C-shape portion to accommodate and clip onto endoscope 2212. The clip 2204 also has a lumen to accommodate the catheter 2224. The lumen of the clip 2204 is offset away from the C-shape portion such that a first air gap 2206 is created between the catheter 2224 and the endoscope 2212. The first air gap 2206 provides thermal insulation by physically separating the endoscope 2212 from the catheter 2224. The lumen runs parallel with a longitudinal axis of the cap 2202 and with a longitudinal axis of the clip 2204. The lumen may match the outer diameter of a catheter for use with the system such as, for example, a cryospray catheter. The extension contains a second air gap 2208 internally that also thermally isolates the catheter from the endoscope. The combined width of the overall assembly at its widest point may be, for example, about 18 mm. The cap may have a maximum diameter of approximately 14 mm exclusive of molded transitions to the fluid supply lumen. The cap 2202 may overhang circumferentially around the endoscope by, for example, about 2 mm to about 4 mm, which contributes to the first gap 2206.

Figure 23A:
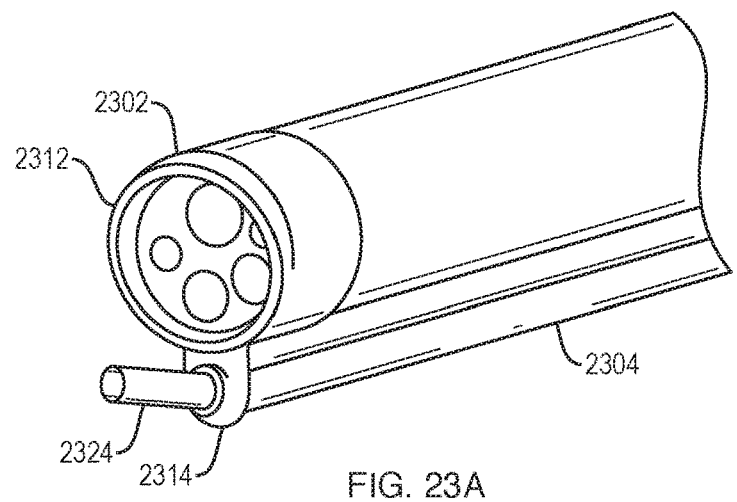
FIGS. 23A-23C depict a multilumen sheath and a cap according to an embodiment of the present disclosure.
Figure 23B:
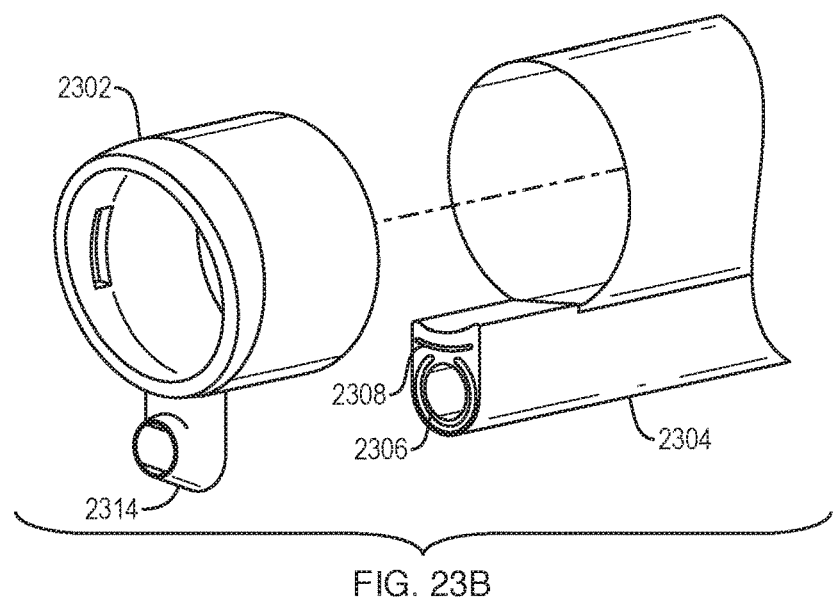
Figure 23C:
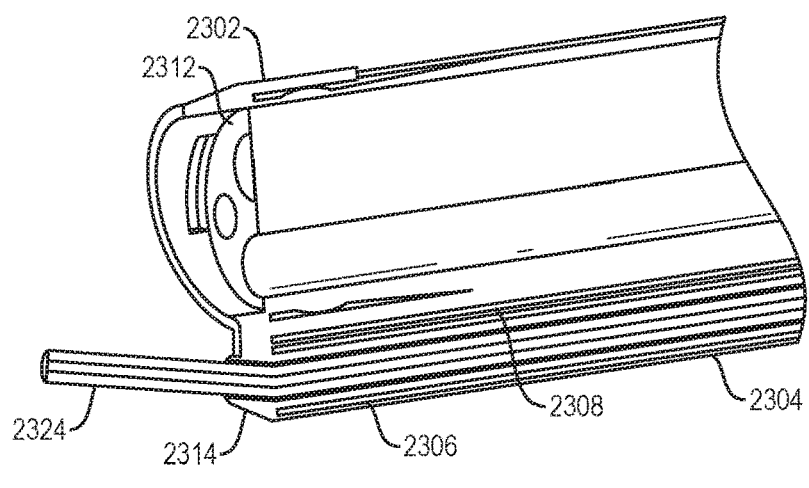

In various embodiments, the system may include an elongate multilumen sheath to accept an endoscope and a catheter with gaps to assist with thermal isolation. A cap may be mounted to the distal ends of the lumens of the multilumen sheath. An external working channel may be insulated and configured to receive a catheter with a sealed air channel or a vacuum gap that provides thermal insulation. For example, FIGS. 23A-23C depict a system with an elongate multilumen sheath 2304, which has a larger lumen for accepting an endoscope 2312 and a smaller external working channel that is a lumen that runs parallel to the larger lumen for accepting a catheter 2324. The cap may be configured, as in any of the embodiments described above, or as otherwise within the scope of the present disclosure, and may be mounted at the distal portion of the larger lumen of the elongate multilumen sheath 2304. The elongate multilumen sheath 2304 includes a first air gap 2306 that is horse-shoe shaped and substantially surrounds the smaller lumen of the multilumen sheath 2304. The elongate multilumen body 2304 also includes a second air gap 2308 that is located between the first air gap 2306 and the longitudinal axis of the larger lumen. The catheter 2324 is outside of and away from the endoscope 2312, which keeps each thermally insulated from the other. Additionally, the first air gap 2306 and second air gap 2308 assist in thermally insulating the catheter 2324 from the endoscope 2312. Any embodiment of a cap of the present disclosure may include an extension with a lumen to accommodate an end portion of the catheter. The cap may mount onto the distal portion of the larger lumen of the multilumen body 2304, while the extension 2314 may mount on the smaller lumen. The lumen of the extension 2314 may be angled towards the longitudinal axis of the larger lumen of the multilumen sheath 2304 such that the catheter 2324 bends towards the endoscope 2312 to be closer within the field of vision of the lens of the endoscope 2312.

Figure 24:
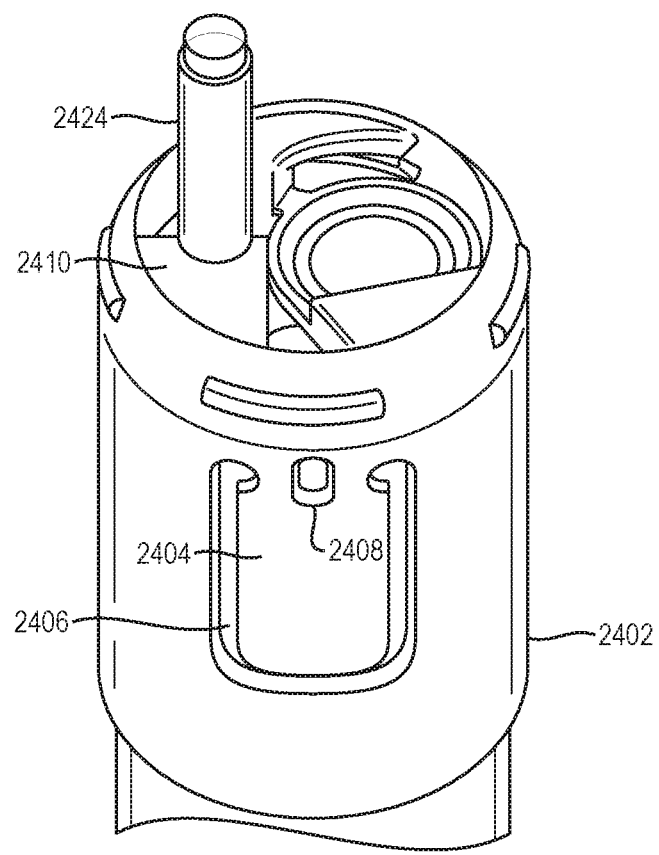
FIG. 24 depicts a cap according to an embodiment of the present disclosure.

In various embodiments, a system may include a seal protecting a working channel of the endoscope, as well as mounting features in the cap. For example, referring to FIG. 24, the system includes a cap with a support rigid plastic tab 2404 with a U-shaped channel 2406 and a notch 2408. Tab 2404 deflects outward when mounted onto the endoscope and clamps the cap 2402 around endoscope with an amount of pressure that does not damage the endoscope. A bump (not shown) on the underside of tab 2404 may be included to provide an interference with the endoscope outer diameter. The notch 2408 may line up with a bump on the endoscope to lock the cap 2402 into place and facilitate proper alignment of the cap 2402 on the endoscope. The cap 2402 may have an outer diameter of, for example, about 12.5 mm. Alternatively, or additionally, inner ribs may be within the cap to provide an interference fit with the endoscope.

During endoscopic and bronchoscopy procedures with spray cryotherapy, the working channel of the endoscope is often subjected to mucus, soft tissue spatter and other liquids that may enter the length of the working channel. This is particularly problematic for cryotherapy procedures as these materials have direct contact with the catheter delivering the cryogen. The direct contact with the additional thermal mass causes a decrease in cryotherapy performance as the output of the catheter is significantly reduced. In some embodiments, a working channel seal may be included with the cap to provide a substantially fluid-tight seal around a catheter or other tool within the working channel of the endoscope. For example, in FIG. 24, a low durometer working channel seal 2410 is disposed around the working channel of the cap 2402 to prevent fluid ingress into the working channel. The seal 2410 may be elastic and designed for interference with a catheter shaft 2424, or may rely on a garter spring to hold the sealing material tight against the shaft 2424. The seal 2410 may be a radial o-ring, or other suitable configuration or material to accomplish the intended sealing and/or wiping effect.

The seal may be made of, a soft polymer material that conforms to the outer diameter of the catheter and that is large enough to seal the entire working channel. As this feature covers the working channel and conforms to the catheter outer diameter, the amount of space for mucus or fluid ingress is drastically reduced or eliminated. The feature may be an o-ring that is appropriately sized (e.g., having an outer diameter larger than a working channel, and an inner diameter just undersized to a catheter outer diameter in order to provide a substantially fluid-tight fit). In addition, the seal may comprise a soft polymer material that can be formed to any shape so that it covers the working channel without blocking other endoscope features. A seal can have a self-sealing feature, e.g., a small cut or slit that allows a catheter to be pushed through it and seal around the catheter outer diameter, and then reseal itself when the catheter is removed.

Alternatively, or in addition, rigid or flexible wiping features may be molded or attached to a catheter's distal outer diameter that allow a catheter to pass through, pushing out fluids during insertion and blocking the majority of the working channel opening from ingress of fluids once in working position.

Figure 25B:
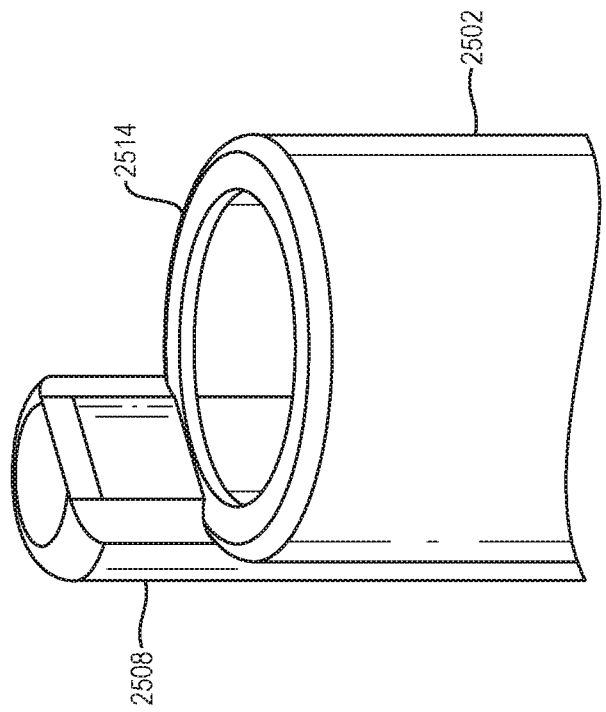
FIGS. 25A and 25B depict a cap according to another embodiment of the present disclosure.
Figure 25A:
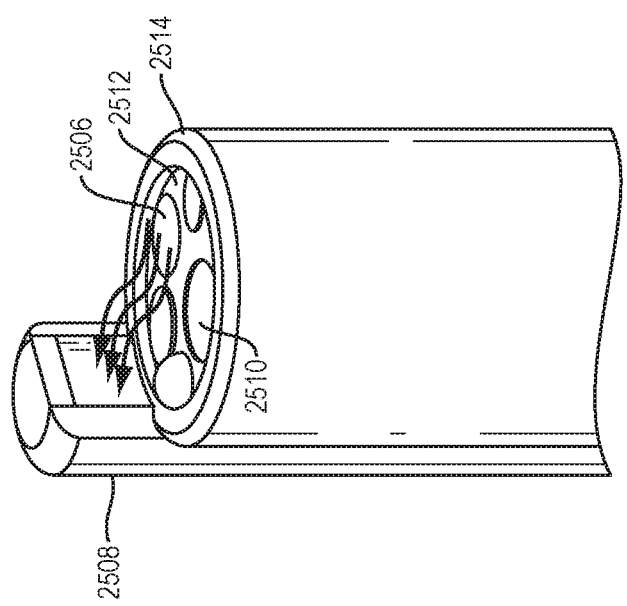

In various embodiments, a cap includes an inner lip to contain an endoscope, the cap includes an egress channel to evacuate the purging fluid, and a working channel within the endoscope supplies the purging fluid. For example, referring to FIGS. 25A and 25B, a cap 2502 is slidingly disposed onto endoscope 2512 and extends along the length of the endoscope 2512. The cap includes an inner lip 2514 at the distal end of the cap 2502 such that the endoscope 2512 may not translate distally past the lip 2514 and thus past the cap 2502. The cap 2502 includes an egress channel 2508 that is a lumen that runs parallel to a longitudinal axis of the cap 2502. The egress channel 2508 extends distally past the lip 2514 of the cap 2502 exposing a radial aperture that is oriented generally towards the center of the cap 2502. A channel 2506 within endoscope 2512 that is slidingly inserted into the cap 2502 supplies a lens clearing purging fluid to the distal end of the endoscope 2512. The cap 2502 may be rotated about the endoscope 2512 such that the egress channel 2508 is positioned on an opposing side of the lens 2510 from the channel 2506 supplying the purging fluid. The egress channel 2508 may be connected at a proximal end to an active suction mechanism to draw the purging fluid from the channel 2506, across the lens 2510, and into gas egress channel 2508.

Figure 26:
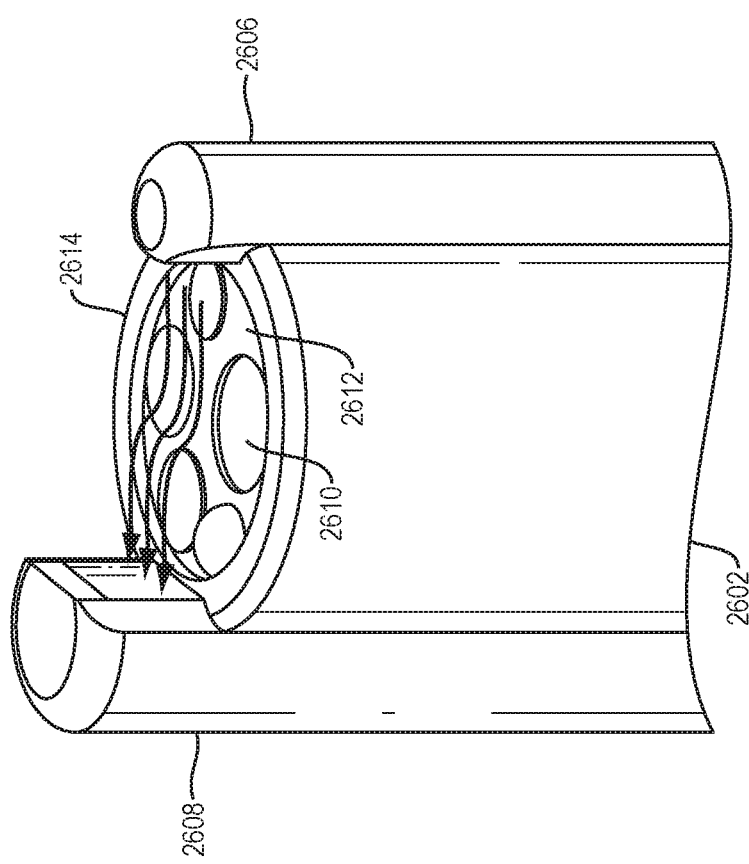
FIG. 26 depicts a cap according to yet another embodiment of the present disclosure.

In various embodiments, a cap includes an inner lip to contain an endoscope, an egress channel to evacuate the purging fluid, and a purging fluid supply mechanism apart from a channel of an endoscope that supplies the purging fluid. For example, referring to FIG. 26, cap 2602 is slidingly disposed onto an endoscope 2612 and extends along the length of the endoscope 2612. The cap includes an inner lip 2614 at the distal end of the cap 2602 such that the endoscope 2612 may not translate distally past the lip 2614 and thus past the cap 2602. The cap 2602 includes a purging fluid supply mechanism 2606 that is a lumen that runs parallel to a longitudinal axis of the cap 2602 to supply the purging fluid. The purging fluid supply mechanism 2606 extends distally past the lip 2614 of the cap 2602 exposing a radial aperture that is oriented generally towards the center of the cap 2602. The cap 2602 includes an egress channel 2608 that is a lumen that runs parallel to a longitudinal axis of the cap 2602 generally opposing the purging fluid supply mechanism 2606. The egress channel 2608 extends distally past the lip 2614 of the cap 2602 exposing a radial aperture that is oriented generally towards the center of the cap 2602. The egress channel 2608 extends distally past the distal end of the purging fluid supply mechanism 2606. The purging fluid supply mechanism 2606 and the egress channel 2608 are positioned such that the lens 2610 of the endoscope 2612 lies between the purging fluid supply mechanism 2606 and egress channel 2608. The egress channel 2608 is connected at a proximal end to an active suction mechanism. The suction draws the purging fluid from the working channel 2606 and across lens 2610 to clear the lens and improve visibility, and into gas egress channel 2608. The egress channel 2608 may also merely use passive venting rather than active suction since the purging fluid supply mechanism 2606 is supplying the purging fluid in the general direction of the egression channel 2608. Egress channel 2608 may extend distally beyond the purging fluid supply mechanism 2606 and include an aperture that is larger than a nozzle or aperture that receives the purging fluid from the supply mechanism in order to capture the purging fluid that may not travel directly across the endoscope 2612 towards the egress channel 2608.

In addition to the features described above, exemplary embodiments may also incorporate heating elements or other forms of temperature control, which are described in more detail in the next section.

Temperature Control

As noted above, embodiments of the visualization system, e.g., systems for use with cryospray catheters, may incorporate a temperature control system, such as an active heater or a passive catheter vacuum jacket. The heating element may maintain safe exposure temperatures in a patient, while maintaining the lens temperature above the dew point.

Figure 7:
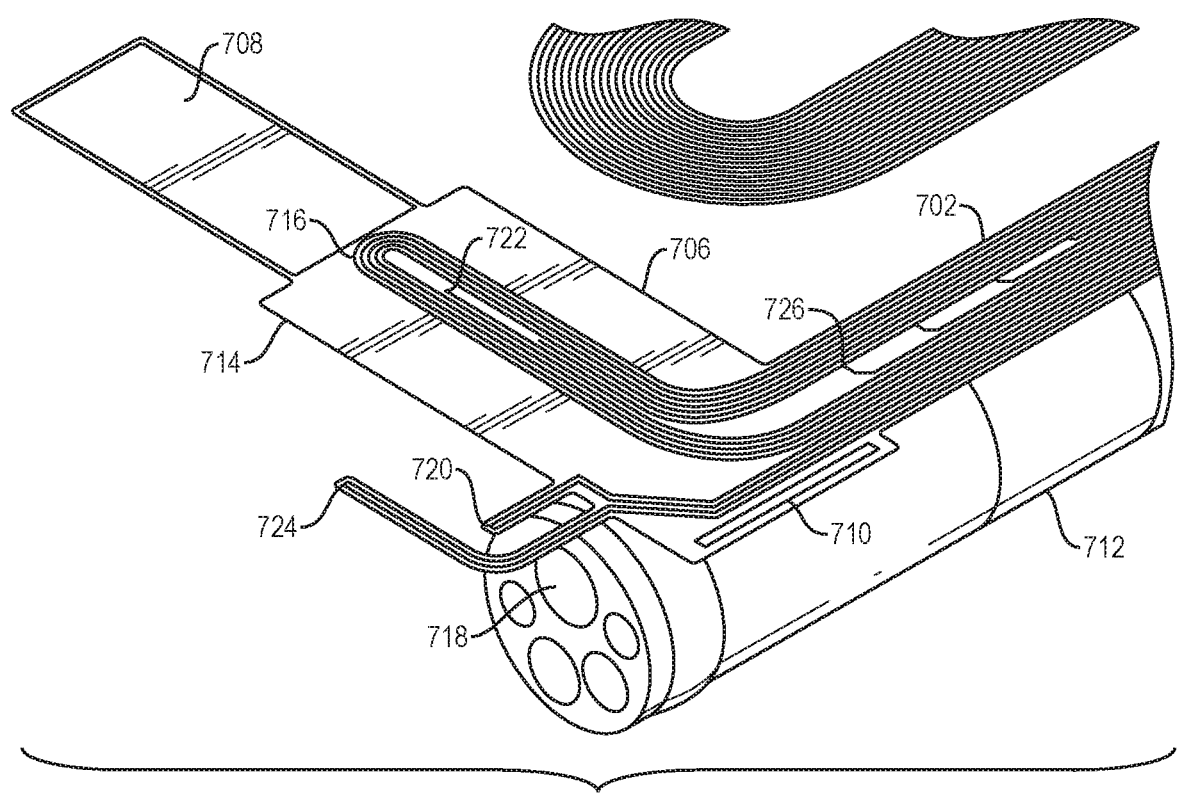
FIG. 7 depicts a heating system according to an embodiment of the present disclosure.

For example, referring to FIG. 7, an embodiment of a temperature control feature according to the present disclosure includes a flexible printed circuit 702 attached to an endoscope 712. The circuit may be attached to endoscope 712 with various means include heat shrink material or adhesive. A flexible printed circuit may electrically heat an endoscope and/or the purging fluid supply mechanism to avoid condensation/freezing temperatures. A flexible printed circuit may run along the length of the endoscope, as shown, and/or along the purging fluid supply mechanism, such that purging fluid is adequately heated when it reaches the cap.

Embodiments of circuits may incorporate temperature sensing elements such as thermocouples, resistance temperature detectors (RTDs) or thermistors to provide control feedback to the power supply. The circuit may also include thermal interface materials to reduce thermal impedance between the heating element and the endoscope and/or purging fluid supply line. Inline heating elements may be provided with a resistive heater or a defrost heater included in the console, as described below.

With further reference to FIG. 7, as an example, the flexible heater/sensor circuit 702 is attached to endoscope 712 by wrapping the distal "flag" 706 around the cylindrical insertion end of the endoscope 712, looping a tab 708 through a slot 710 and pulling taut to compress a gap pad 714 (underside, not shown in rendering), then securing the tab 708 back onto flag 706 using pressure sensitive adhesive pre-applied to the back of tab 708.

In an alternative embodiment, tab 708 and slot 710 are eliminated, the circuit 702 is adhered to or printed onto the inside diameter of a heat shrinkable material (e.g., polyolefin, PET, PFA, PVC, etc.), and circuit heating element 716 is used to shrink the circuit down onto an endoscope 712 to provide a secure temporary fit. A heat shrink band may be perforated along the longitudinal axis for ease of removal after use, similar to a quality seal used on medicine bottles. Gap pad 714 is used to create a low impedance thermal connection between the heater coil 716 and the endoscope 712 to provide necessary heating to maintain a lens 718 above the dew point without reaching excessive temperature on the external (patient contacting) diameter of the assembly.

To the same end of limiting patient exposure temperature, the outside diameter of the assembly is insulated with either heat shrink sleeving, or insulated by an embodiment of a distal cap attachment as described herein, which is applied over the heater/sensor circuit 702 assembly. The leads to the heater/sensor circuit 702 may be constrained along the length of endoscope 712 using, for example, clips similar to the ones shown in FIGS. 2A-2D, or by using pressure sensitive adhesive pre-applied to a sheet of the circuit, or by using a heat shrinking sleeve as previously described. These and various other attachment means may be used with other configurations of circuits or with other types of temperature control features to secure the sensor/heater to the scope, catheter, or cap attachments.

With further reference to FIG. 7, as an example, heating element 716 is powered by a DC voltage source, either within, e.g., a cryospray console or as a separate power controller. In some embodiments, the heating element may be thermostatically controlled. The heater power may be PID loop controlled, where the process variable is the lens 718 temperature as measured by self-adhesive temperature sensor (e.g., thermocouple, RTD, or thermistor) 720 which is applied to the distal tip of the endoscope 712 by folding such that it sits adjacent to the lens 718.

Temperature sensors 722 are disposed circumferentially around the heating element 716 to assure that even thermal contact is made between the circuit 702 and the endoscope 712, avoiding the risk of hot spots that could exceed rated patient exposure temperatures. A sensor appendage 724 is similarly a safety feature containing a temperature sensor which folds back on itself over the applied heat shrink insulation to monitor the external surface temperature which is exposed to the patient. The sensor 712 cuts off power to the heating element 716 if an exposure temperature exceeds a preset maximum. The sensors 722 are compared to one another to determine a standard deviation, and similarly a warning is offered and/or power is cut off if the deviation exceeds a preset maximum. One or more temperature sensors are disposed longitudinally along the endoscope 712 and may be used for experimental data collection. The heater/sensor circuit 702 can be located along an inner layer of the assembly and a purging fluid supply mechanism may be attached/molded to the sheet of the circuit. The entire assembly may be pre-assembled into a tubular capped sleeve which easily slips over the length of the endoscope 712. The assembly may be secured through the use of heat shrinking material using heat provided by heating element 716 for ease of installation prior to a procedure.

Figure 8:
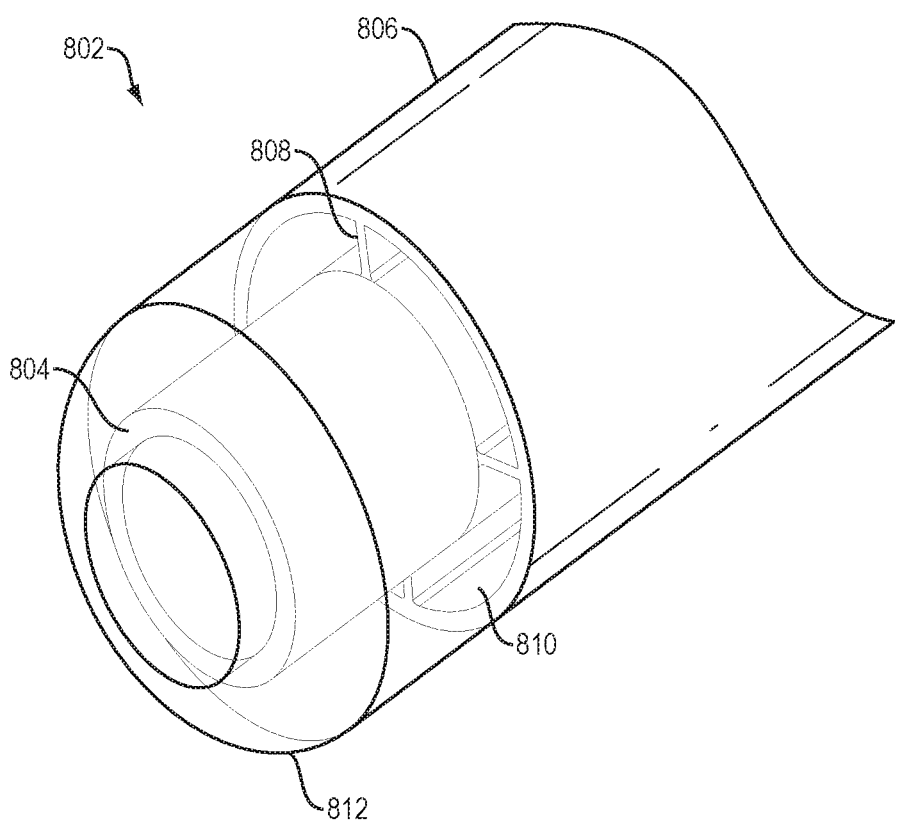
FIG. 8 depicts a catheter vacuum jacket according to an embodiment of the present disclosure.

In various embodiments, a system may include a vacuum jacket that thermally isolates a catheter and an atraumatic tip that maintains the vacuum in the jacket and has a generally rounded tip to avoid damaging a body lumen. For example, referring to FIG. 8, a flexible vacuum jacket 802 is shown on a catheter and/or endoscope (not shown). The catheter vacuum jacket 802 reduces or eliminates convection and reduces or minimizes conduction and radiation on the external surface of the catheter. The jacket insulates the catheter, which may be a catheter for delivering cryospray and allows the endoscope to maintain ambient room temperature. The vacuum jacket 802 may be a polymer extrusion 806 having metalized inner surfaces for radiation shielding that allow for a permanent or semi-permanent vacuum to be held without outgassing of the polymer substrate. The extrusion 806 may include vacuum channels 810 that are evacuated lumens separated by thin ribs 808 that may be made of a material such as polyethylene terephthalate or nylon. An inner lumen 804 may contain a catheter and/or endoscope. The inner lumen 804 separates the catheter and/or endoscope from the vacuum created by the jacket 802. The inner lumen 804 may be made of a polyimide material. An atraumatic tip 812 may surround the inner lumen 804 to maintain the sealed vacuum and protect an end of the catheter and/or endoscope. The atraumatic tip 812 includes a lumen that may match with the inner lumen 804, such that medical tools, or a catheter, or an endoscope may access a target site within a patient. The jacket may include either additionally or alternatively, annular metal tubes separated with low conductivity spacers disposed along the length of the jacket to maintain separation between inner and outer tubes. These tubes can be welded or bonded at both ends to create an evacuated space. The metal tubes may be made of, for example, stainless steel or nitinol.

Applications: Cryosurgery Systems

Figure 9:
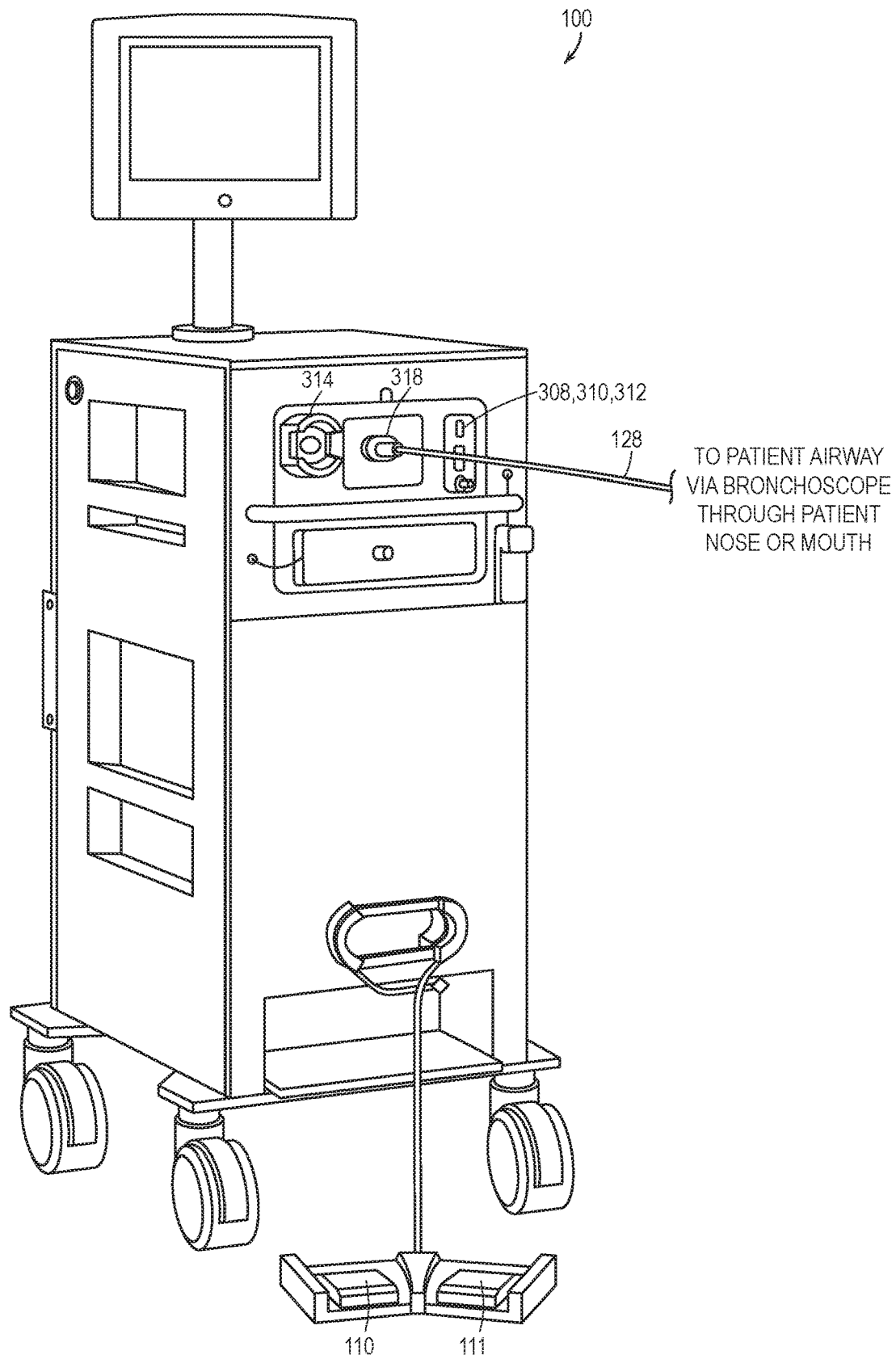
FIG. 9 depicts a perspective view of an exemplary cryosurgery system that may be employed with a visualization system according to embodiments of the present disclosure.
Figure 10:
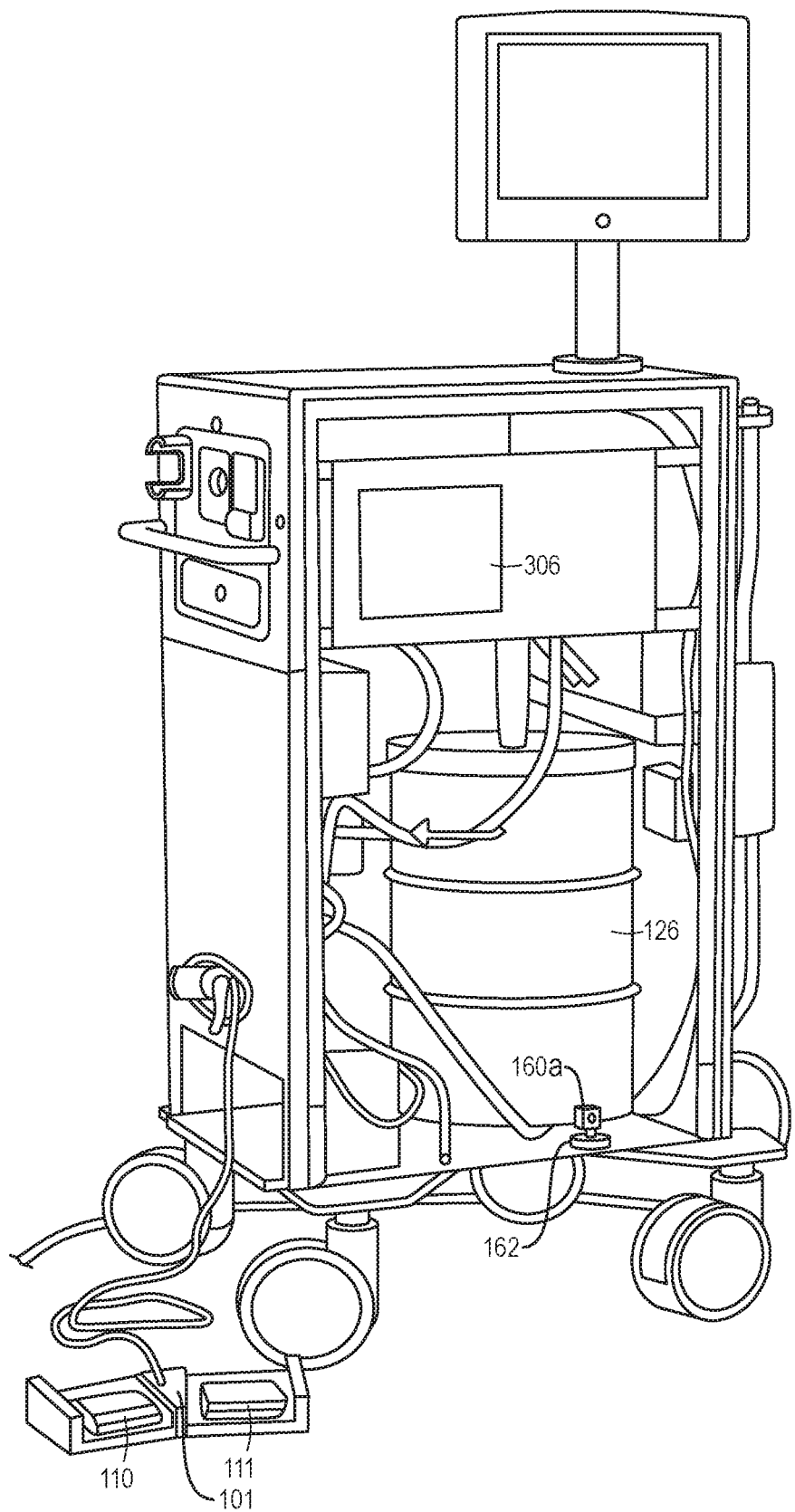
FIG. 10 depicts a perspective view of an interior of an exemplary cryosurgery system that may be employed with a visualization system according to embodiments of the present disclosure.

The visualization systems described above may be employed in connection with any type of visualization means, such as an endoscope, and with any type of tool used with such visualization means. The visualization systems of the present disclosure are particularly well-suited to application in cryogenic medical systems, such as cryosurgery systems, and most particularly with cryospray catheter systems. For example, a simplified perspective view of an exemplary cryosurgery system in which embodiments of the present disclosure may be implemented is illustrated in FIGS. 9-10. It should be noted that one or more of the features described here could be applicable to other configurations of cryosurgery systems for use with any visualization system according to the present disclosure. A cryosurgery system 100 may comprise a pressurized cryogen storage tank 126 to store cryogen under pressure. In the following description, the cryogen stored in tank 126 is liquid nitrogen although other cryospray may be suitable. The pressure for the liquefied gas in the tank 126 may range from 5 psi to 55 psi. For example, when the pressure in the tank during operation is set to 20 psi, the flow rate/cooling capacity of the nitrogen may be 25 W. Liquid nitrogen (LN2) resides on the bottom of the tank 126 and liquid nitrogen gas/vapor (GN2) occupies the top portion of the tank 126. Tank level is monitored electronically via a sensor internal to the tank 126 that changes value with the level of the liquid inside the tank 126.

The console depicted in FIG. 9 includes an emergency shut off 314, pressure sensor port 308, temperature sensor port 310 and digital input port 312. An interface 318 is a secure connection point for the delivery apparatus 128 to the console, such as a mating receptacle for a probe connector, such as bayonet 1202 of the probe depicted in FIGS. 12 and 15. The console may include an RFID tag reader 306 to identify each probe as it is used and in the case of a disposable unit, ensure that each probe is only used once per procedure. Foot pedals may be included with system 100 to allow for convenient control of cryogen flow with pedal 110 and suction with pedal 111. However, suction does not have to be connected to the console or included as a necessary feature of the system.

Figure 11A:
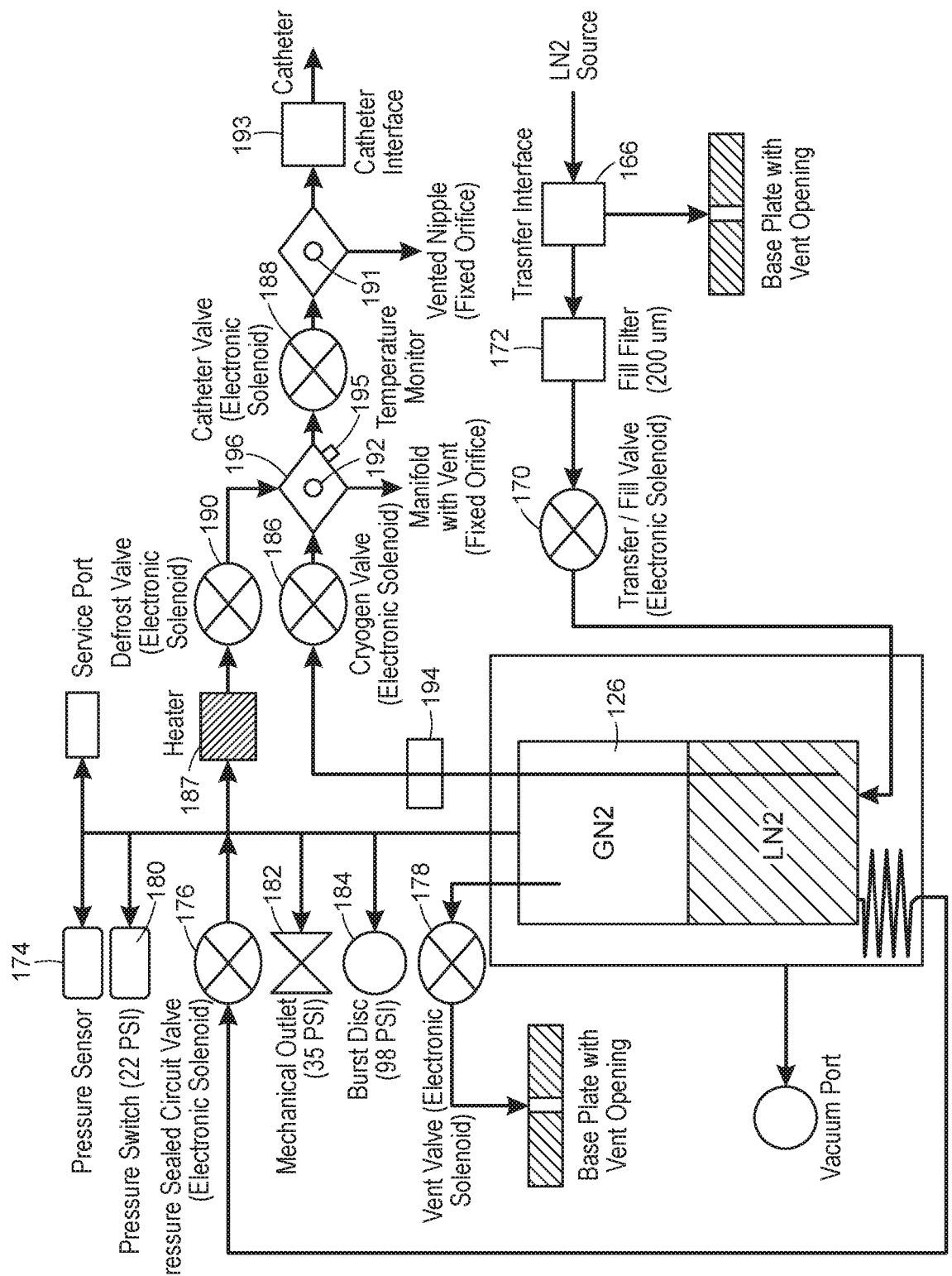
FIG. 11A is a schematic showing a cryogen storage, delivery and pressure control apparatus of an exemplary cryosurgery system that may be employed with a visualization system according to embodiments of the present disclosure.
Figure 11B:
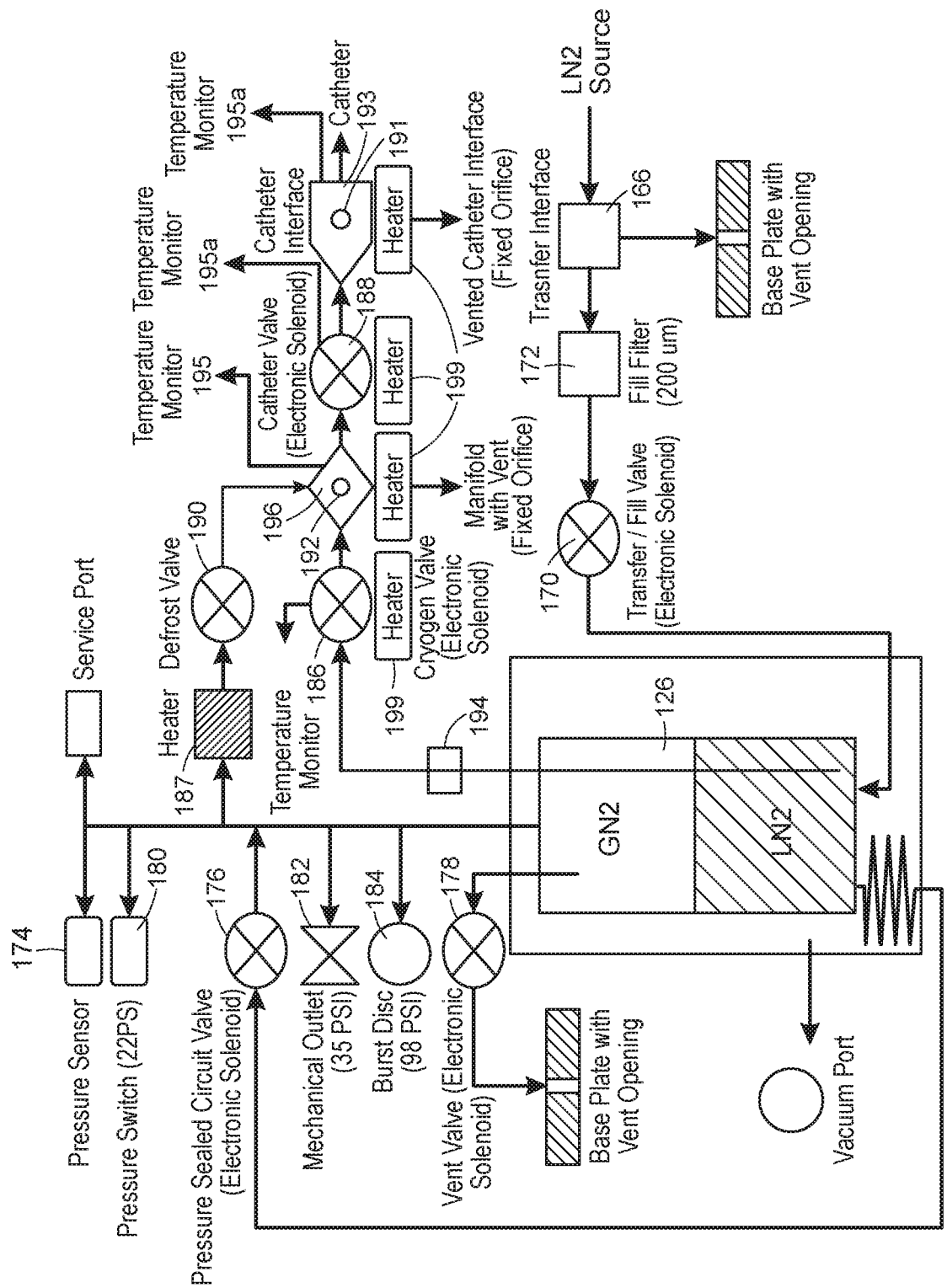
FIG. 11B is a schematic showing a cryogen storage, delivery and pressure control apparatus of an exemplary cryosurgery system that may be employed with a visualization system according to embodiments of the present disclosure.

Referring to FIGS. 11A and 11B, exemplary embodiments may continuously monitor and control the pressure of liquid nitrogen in the tank during use. The console monitors the current pressure of the tank via a pressure sensor 174. The software reads the current pressure from the sensor and adjusts the pressure accordingly. If pressure is too low, the software actuates the pressure build circuit valve 176 to increase the pressure to a specified threshold and then turns off. When the pressure is too high, the software turns on the vent valve 178 until the pressure reaches a specified threshold.

A mechanical relief valve 182 on the console tank ensures that the tank pressure stays in a safe pressure range. A redundant burst disk 184 provides protection should the mechanical relief valve fail. In addition, a redundant pressure switch 180 may provide accurate tank pressure readings and is checked during the self-test.

A cryospray system may utilize a manifold assembly, e.g., such as cryogen valve 186, manifold 196, catheter valve 188, defrost valve 190, fixed orifices 191 and 192, and catheter interface 193 of FIGS. 11A and 11B, to control liquid nitrogen delivered through a catheter. In the assembly shown, when the cryogen valve 186 is actuated, liquid nitrogen exits the tank through the lance 194 and proceeds through the cryogen valve 186 to manifold 196 where fixed orifice 192 is present to allow cold expanded gas and liquid cryogen to exit the line and cool down the internal cryogen circuit. During this precool, the catheter valve 188 downstream of the manifold remains closed. A data acquisition board collects data from a thermocouple 195 located on the manifold body. In the precool function, the system software monitors data from the thermocouple 195, and opens the cryogen valve 186 to cool the manifold 196 when its temperature is above the desired set-point. According to one embodiment, fixed orifice 191 is provided on catheter interface 193 to allow venting of cold expanded gas to exit the line while spraying.

According to an embodiment, as represented in FIG. 11B, each of cryogen valve 186, manifold 192, catheter valve 188 and catheter interface 193 are provided with a temperature thermocouple or sensor 195a and a heater 199 to maintain the cryogen flow path at a constant selected temperature to prevent overcooling of the system resulting from the continuous flow of cryogen through the valves and manifold assembly. According to various embodiments, each of the heaters may be controlled to maintain the valves, the manifold and the catheter interface at the same temperature or at different temperatures.

A defrost function is useful for thawing a catheter after cryogen spray, before removal from the endoscope. In the example of FIGS. 11A and 11B, a defrost circuit directs gaseous nitrogen from the top of the tank through a heater 187 and defrost valve 190 to the catheter 128. When the defrost button on the software screen is pressed, the defrost circuit is activated for a prescribed time (e.g. 30 seconds) but can be stopped earlier at the user's discretion. A low voltage (24 VDC) DC defrost heater delivers 6 W minimum of warming/defrost performance. In various embodiments, a temperature sensor may be included in a system on a catheter to provide control feedback to a console that regulates flow from a cryosource in order to maintain a certain temperature and/or cryogen dosage.

Figure 12:
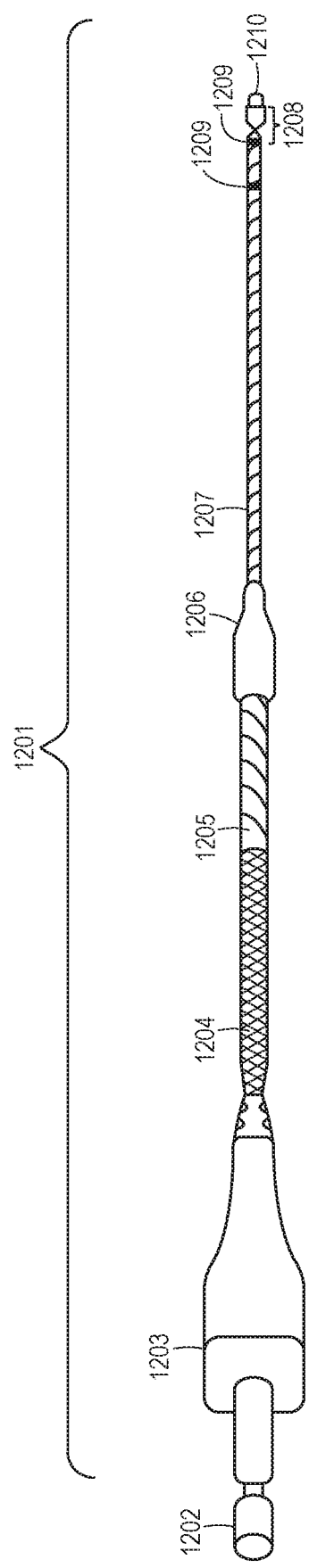
FIG. 12 depicts an isometric view of an exemplary radial spray catheter for a cryosurgery system that may be employed with a visualization system according to embodiments of the present disclosure.

FIG. 12 depicts an exemplary catheter 1201 designed to transport liquid nitrogen (or other cryogen) from the console to the patient treatment site. According to this embodiment, the catheter 1201 contains a bayonet 1202 and a hub 1203 for attachment to the console at its proximal end, a laser cut hypotube 1205 to minimize kinking and breaking, which is laminated by a heat shrink wrap (or secured by other means, such as by coating with a polymer jacket applied using a dip process) to seal the fluid flow and for insulation, an insulation layer 1204 to protect the user from cold temperatures, a nozzle connection of diminishing inner diameter 1206, a second smaller ID laser cut hypotube 1207 with FEP or Pebax heatshrink wrap, a catheter/needle head 1208, marking band 1209, and a closed distal end 1210.

Figure 15:
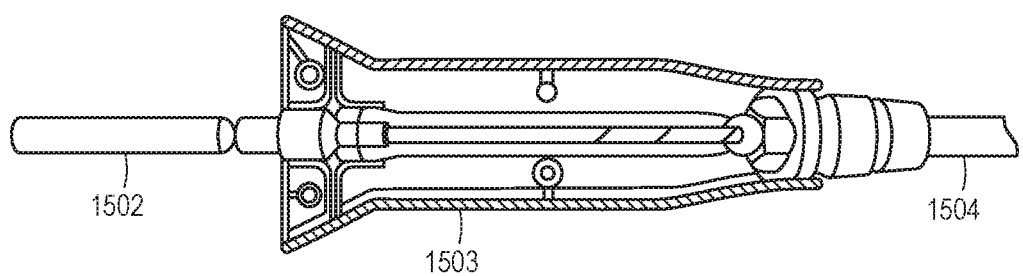
FIG. 15 depicts an insulator and connector housing area with a bayonet connector for an exemplary cryospray catheter for a cryosurgery system that may be employed with a visualization system according to embodiments of the present disclosure.

FIG. 15 depicts an insulator 1504 and an exemplary cross-section of a hub 1503 with a bayonet 1502 at the proximal end of a catheter assembly for attachment to a cryogen source. A hypotube design and construction provides additional strength and flexibility, allowing the physician to retroflex the catheter during a treatment procedure, if needed.

A catheter package in various embodiments may contain an RFID tag that the user scans prior to use to prevent reuse and track disposable information. The catheter package may also contain an introducer that provides reinforcement for the catheter and helps prevent kinking during use and when placing the catheter into the endoscope. An alternative construction locates the RFID tag on the connector area adjacent to the bayonet. A bayonet connector may include a thermocouple connection that connects a thermocouple on the catheter to a console.

In various embodiments, a delivery catheter may be constructed out of hypotubes of different internal diameters mated to each other to make a proximal shaft and a distal shaft, with the distal shaft containing the smaller internal diameter. The proximal and distal shafts may be joined at a connector. The proximal shaft may contain a bayonet and hub for attachment to the console at its proximal end. The distal shaft preferably has a reduced internal diameter to be able to fit through the working channel of an endoscope, such as a bronchoscope. A distal tip of the catheter may contain radial spray pattern holes which make up the nozzles configured to deliver cryogen spray onto target tissue. The end of the catheter may be configured to have rounded tip, preferably made of a welded stainless steel sphere. This rounded tip may help reduce trauma to the tissue during catheter insertion or manipulation into the body cavities. A thermocouple may be included along the catheter shaft, preferably at or near the distal tip of the catheter, to provide temperature feedback to the control console, for example to better determine and control cryospray dosing and temperature at the tip of the catheter. The hypotubes may be all laminated with a polymeric heatshrink which seals the shaft, or seals a portion of the shaft such as a laser cut pattern, from the liquid intended to flow inside the catheter. Additionally, both hypotubes may have variable laser cut patterns to provide rigidity where needed and allow flexibility where needed. This is accomplished by varying the separation of the spiral or repeated cut pattern, as well as varying the shape of the pattern itself.

In various embodiments, within the scope of the present disclosure, a delivery catheter may be constructed of three layers of flexible polyimide, surrounded by a stainless steel braid, which is in turn coated with an outer layer of Pebax. An extrusion of Pebax over the stainless steel braid may allow the Pebax to wick through the pitch of the steel braid, helping to prevent kinking, breaking, or delamination during retroflex of the catheter. The Pebax also provides a desirable balance between hardness, important for smooth sliding of the catheter and general toughness, and softness, which is important for some degree of tackiness to allow the user to feel the movement of the catheter in the endoscope. The pitch of the stainless steel braid is configured to be fine enough to afford the required strength, but still allow the Pebax to wick through. The distal end of the catheter may be provided with an atraumatic tip comprised only of Pebax, in the shape of a bullnose. This construction allows for retroflex of the catheter without kinking, breaking, or delamination of the catheter. For the purposes of this disclosure, retroflex is used to refer to the ability of a catheter to bend or turn approximately 210° about a radius of curvature of 0.375 inch or greater.

By adding very thin layers of metal to a catheter shaft or increasing the heat transfer coefficient in the shaft by using a hypotube or adding a braided metal for example, a catheter may be constructed to provide optimal cryo delivery to the tip of the device in a very short cycle time.

Figure 13:
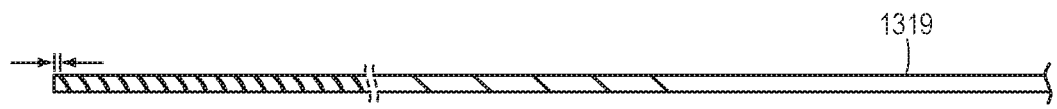
FIG. 13 depicts a side view of an exemplary cryospray catheter for a cryosurgery system that may be employed with a visualization system according to embodiments of the present disclosure.

FIG. 13 depicts an exemplary catheter shaft for a cryosurgery system with a hypotube 1319 that may be used for the construction of the proximal end of the catheter shaft 1205. In various embodiments, it may have a length of approximately 45 inches, but can vary from 10 inches to 100 inches in length. The internal diameter of the tube 1319 may be approximately 0.104 inches (3.56 mm), but can vary from 0.031 inches to 0.197 inches (0.8 mm to 5 mm), preferably from 0.039 inches to 0.157 inches (1 mm to 4 mm). The hypotube 1319 may be, as shown, laser cut as a spiral, but other variable cuts can be present to provide desired flexibility/rigidity along the length of the tube.

Figure 14:
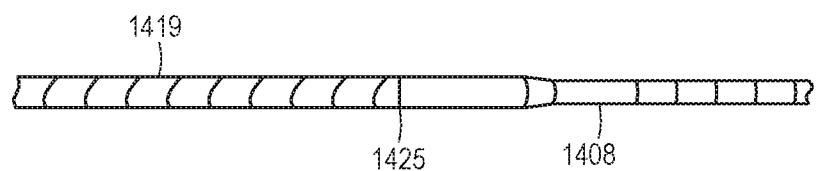
FIG. 14 depicts a side view of an exemplary cryospray catheter construction for a cryosurgery system that may be employed with a visualization system according to embodiments of the present disclosure.

FIG. 14 depicts an exemplary catheter shaft for in a cryosurgery system with a transition 1425 of a larger diameter hypotube shaft 1419 to a smaller diameter laser cut hypotube shaft 1408. The transition may be configured so that a smaller diameter may be inserted for example into the working channel of an endoscope or trocar. In addition, the transition from large diameter to small diameter may act as a mixing point for dual phase flow gas and liquid to interact along the path of the catheter shaft and allow for the gas to once again attain the velocity of the liquid as the dual phase flow travels down the shaft. This is understood by those skilled in that art as a "nozzling" transition.

Control of cryogen suited to desired treatment applications and parameters may be achieved in accordance with the present disclosure through a "nozzle" flow created by tailoring, for example, shafts of a certain length, diameter size and number of transitions. Transitions may occur between two hypotubes, two polymeric shafts or between a coil and hypotube or coil and polymeric shaft.

Figure 16:
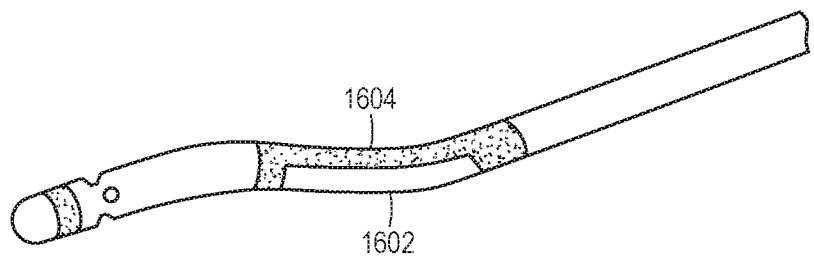
FIG. 16 depicts an S-curve centering feature of an exemplary cryospray catheter for a cryosurgery system that may be employed with a visualization system according to embodiments of the present disclosure.

FIG. 16 depicts an exemplary catheter shaft for a cryosurgery system with an S-curve centering feature built into the distal tip. FIG. 16 shows the bend 1602 and the alignment line 1604 that is the feature used to visually align the catheter with respect to the endoscope working channel offset.

Figure 17:
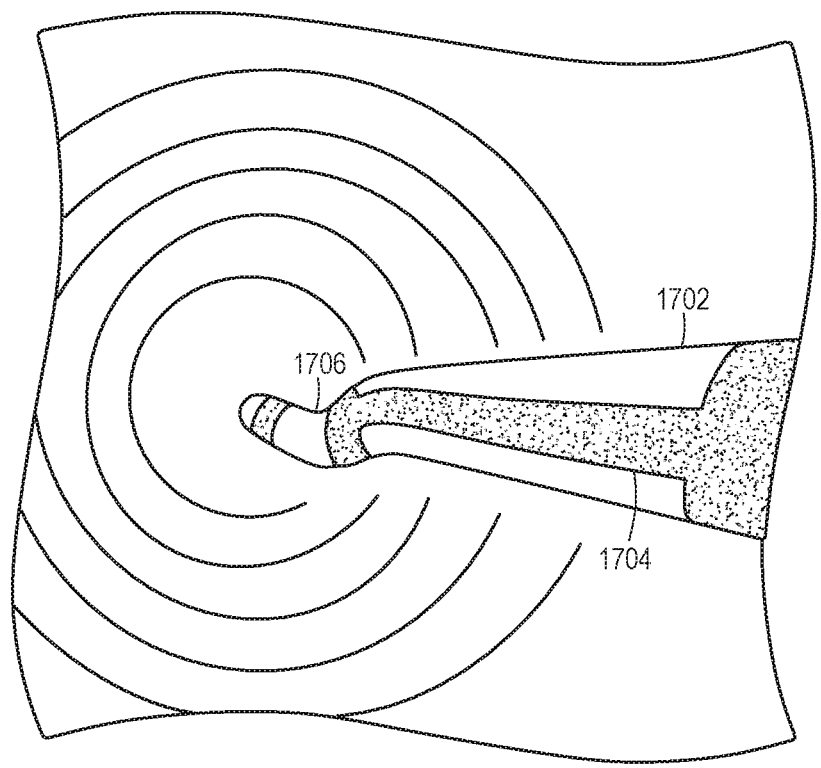
FIG. 17 depicts an S-curve centering feature and axial line as viewed through an endoscope with an exemplary cryospray catheter for a cryosurgery system that may be employed with a visualization system according to embodiments of the present disclosure.

FIG. 17 depicts an exemplary catheter shaft for a cryosurgery system with an S-curve 1702 of an alternate embodiment as seen through an endoscope visualization system. A method of use is to target the area to be treated by locating the catheter section 1706 between the marking bands, then rotating the catheter axially until the axial line 1704 is visible and horizontal in the line of vision. At this point the catheter tip is relatively centered with the endoscope centerline. This axial line is typically created via a pad printed or laser marking process.

Other embodiments of catheter shafts of the present disclosure do not need to include an S-curve feature. Instead, a shaft could include a radial spray head with blunt-tip geometry and one or more radial apertures arranged around a circular atraumatic tip.

An exemplary method of using a visualization system with a cryospray catheter for vision preservation according to the present disclosure includes attaching a cap to an endoscope and inserting a catheter within the endoscope. The method may include supplying a purging fluid to a lens of the endoscope. The method may include supplying cryospray to the catheter. The method may include purging moisture to avoid condensation on the lens, shearing debris and bodily fluids away from the field of view, and/or deflecting spatter from the field of view.

Figure 18A:
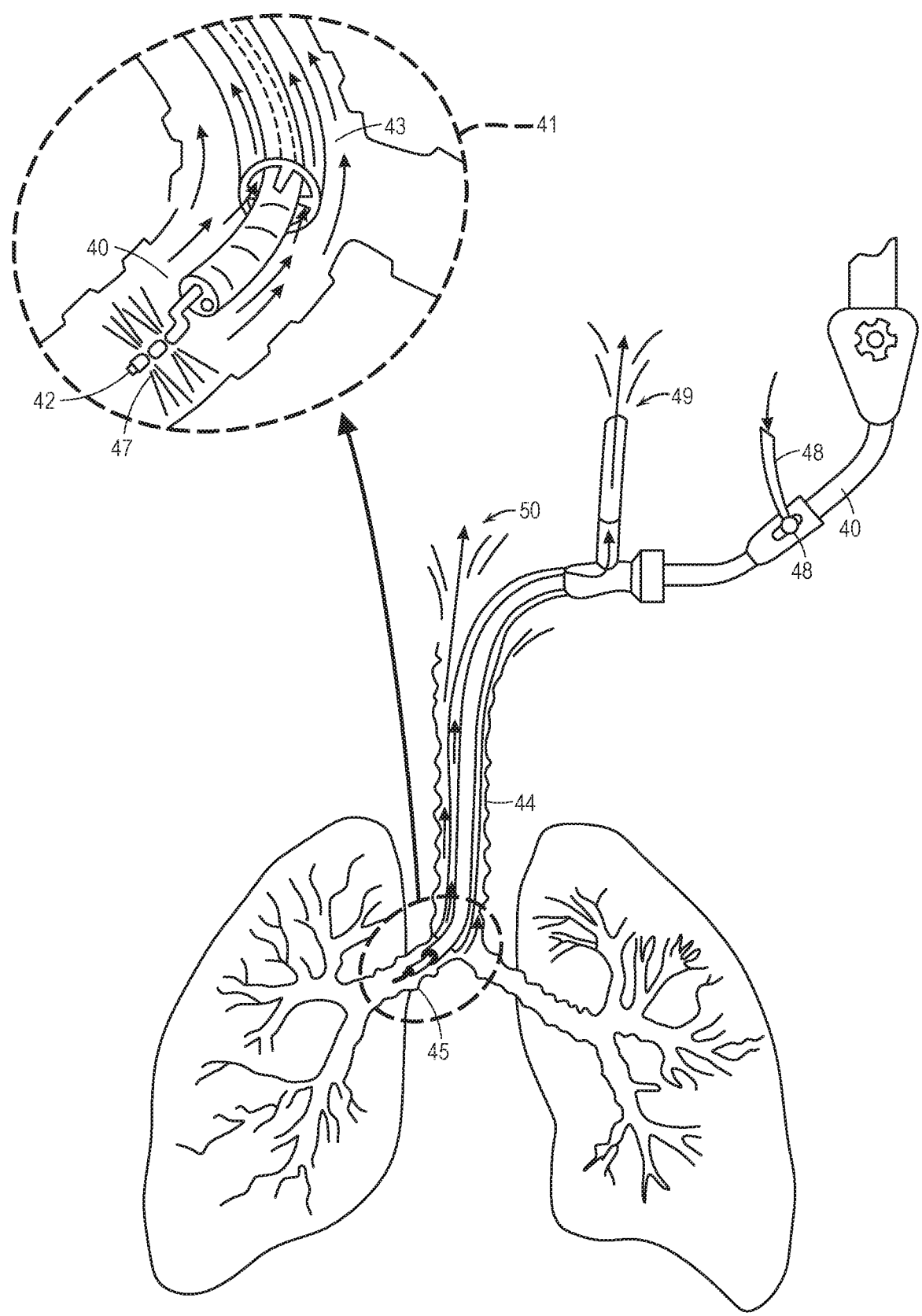
FIG. 18A depicts a perspective view, including a blow-up view, of a portion of a cryosurgery system of an exemplary cryosurgery system that may be employed with a visualization system according to embodiments of the present disclosure.
Figure 18B:
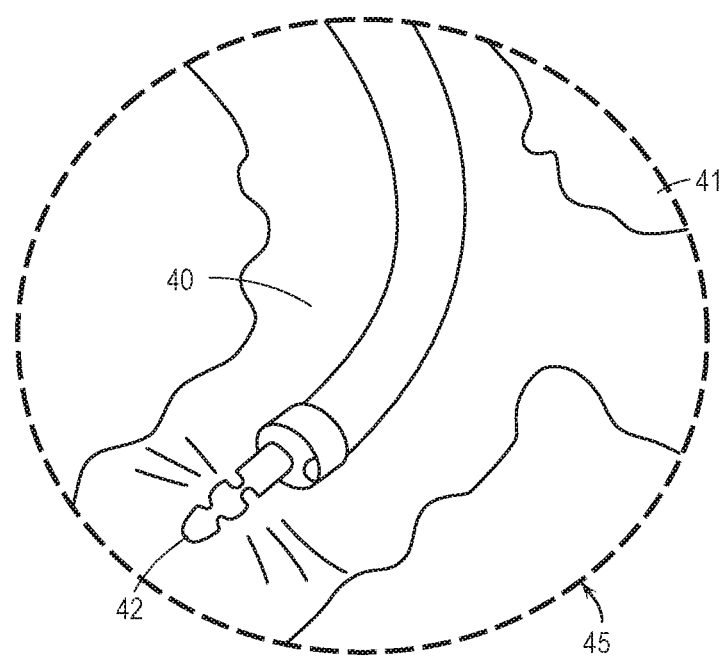
FIG. 18B depicts an exemplary cryosurgery system with a visualization system that may be employed according to an embodiment of the present disclosure.

FIG. 18A depicts an exemplary catheter shaft for a cryosurgery system with a bronchoscope 40 that may be positioned in the trachea 44, or bronchi, such as the principle bronchi 45 of a patient. The catheter 48 is placed in the working channel lumen 46 of the endoscope 40 and exits the working channel at the distal tip of the endoscope. Cryogen delivery apparatus 42 comprises a radial spray cryogen delivery catheter at distal end 42, and one or more holes 47. After insertion of the cryogen delivery apparatus into the patient, cryogen is provided to cryogen delivery catheter 48 from a cryogen source. A gas egress tube 43 that surrounds the endoscope may be utilized to provide additional means to evacuate cryogenic gas from the treatment area out of the patient 49. Passive lumen egress 50 is also present via management of the airway to ensure proper venting during the procedure. FIG. 18B shows a blow-up of an alternate embodiment, in which a straight tipped catheter 42 is used without a gas egress tube.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the endoscope or meaning of the claimed technology.

Certain embodiments of the present invention have described above. It is, however, expressly noted that the present invention is not limited to those embodiments, but rather the intention is that additions and modifications to what was expressly described herein are also included within the scope of the disclosure. For example, although the present Figures may include exemplary dimensions, one of ordinary skill in the art will recognize that these dimensions are provided for the sake of illustration and that other dimensions may be used, depending on the application.

Moreover, it is to be understood that the features of the various embodiments described herein were not mutually exclusive and can exist in various combinations and permutations, even if such combinations or permutations were not made express herein, without departing from the spirit and endoscope of the invention. In fact, variations, modifications, and other implementations of what was described herein will occur to those of ordinary skill in the art without departing from the spirit and the endoscope of the invention. As such, the invention is not to be defined only by the preceding illustrative description.

What is claimed is:

1. A visualization system comprising:
   an endoscope having a lens and a working channel for a tool;
   a cap at least partially surrounding the lens, the cap including an angled partition about the lens; and
   a lens clearing flow field adjustment mechanism for delivering a purging fluid radially across the lens;
   wherein a portion of the angled partition opposes the lens clearing flow field adjustment mechanism from across the lens and is configured to direct a gas phase of the radially delivered purging fluid away from the lens and towards a guide surface of the cap, the guide surface facing substantially towards the angled partition;
   wherein a supply mechanism for the purging fluid is affixed to the endoscope using a heat shrink sleeve, the sleeve comprising circuitry disposed at least partially along the sleeve to provide a self heat-shrinking effect to the sleeve.

2. The visualization system of claim 1, wherein the lens clearing flow field adjustment mechanism is configured to deliver an angled jet of the purging fluid to the lens.

3. The visualization system of claim 1, wherein the purging fluid is phase-separated and the angled partition is configured to direct the phase separated purging fluid delivered to the lens, by directing the gas phase of the purging fluid in a substantially distal direction away from the lens and by directing a liquid phase of the purging fluid in a substantially radial direction away from the lens.

4. The visualization system of claim 1, wherein the cap is asymmetric about an axis extending in a radial direction with respect to a central axis of the cap.

5. The visualization system of claim 1, wherein the cap further comprises a transparent lens.

6. The visualization system of claim 1, further comprising a spatter deflection nozzle provided in the cap for deflecting spatter away from the lens.

7. The visualization system of claim 1, wherein the guide surface comprises a flow deflection guide configured to redirect a flow field of the purging fluid delivered from the lens clearing flow field adjustment mechanism.

8. The visualization system of claim 1, wherein the supply mechanism for the purging fluid is further affixed to the endoscope using one or more of a rubber cuff providing a friction fit or one or more deflecting tabs or clips.

9. A visualization system comprising:
   an endoscope having a lens and a working channel for a tool;
   a cap surrounding the lens, the cap including an angled partition about the lens;
   a lens clearing nozzle provided in the cap for delivering a phase-separated purging fluid radially across the lens; and
   a purging fluid supply mechanism external to the endoscope for supplying the purging fluid to the cap, wherein the purging fluid supply mechanism is affixed to the endoscope using a heat shrink sleeve;
   wherein a portion of the angled partition opposes the lens clearing nozzle from across the lens and is configured to direct a gas phase of the radially delivered purging fluid in a substantially distal direction away from the lens and towards a guide surface of the cap, the guide surface facing substantially towards the angled partition, and is configured to direct a liquid phase of the purging fluid in a substantially radial direction away from the lens.

10. The visualization system of claim 9, wherein the purging fluid supply mechanism is a separate lumen affixed to the endoscope.

11. The visualization system of claim 9, wherein the guide surface is configured to deflect the purging fluid away from the working channel of the endoscope.

12. The visualization system of claim 11, wherein the guide surface comprises a scooped shape that follows a contour around a portion of the perimeter of the cap.

13. The visualization system of claim 11, wherein the guide surface comprises an upper distal edge that is slanted at about 60 degrees from a radial axis of the cap.

14. The visualization system of claim 9, further comprising an opening in the cap opposite to the lens clearing nozzle that is a lumen extending distally from the cap substantially parallel to a longitudinal axis of the cap.

15. A visualization system comprising:
- an endoscope having a lens and a working channel for a tool;
- a cap surrounding the lens, the cap including an angled partition about the lens; and
- a lens clearing nozzle provided in the cap for delivering a purging fluid radially across the lens, wherein the lens clearing nozzle receives the purging fluid from a purging fluid supply mechanism, modifies a flow field of the purging fluid, and directs the flow field towards the lens;
- wherein a portion of the angled partition opposes the lens clearing nozzle from across the lens and is configured to direct a gas phase of the radially delivered purging fluid away from the lens and towards a guide surface of the cap, the guide surface facing substantially towards the angled partition;
- wherein the purging fluid supply mechanism is affixed to the endoscope using a heat shrink sleeve and wherein the purging fluid supply mechanism is further affixed to the endoscope using one or more of a rubber cuff providing a friction fit or one or more deflecting tabs or clips, or a combination thereof.

16. The visualization system of claim 15, wherein the cap is symmetric about an axis extending in a radial direction with respect to a central axis of the cap.

17. The visualization system of claim 15, wherein the cap further comprises an inner lip at a distal end of the cap such that the endoscope may not translate distally past the lip.

* * * * *